(12) United States Patent
Radu et al.

(10) Patent No.: US 11,121,324 B2
(45) Date of Patent: Sep. 14, 2021

(54) DIHETERO AMINES IN ELECTRICALLY CONDUCTIVE POLYMER COMPOSITIONS

(71) Applicant: LG Chem, Ltd., Seoul (KR)

(72) Inventors: Nora Sabina Radu, Landenberg, PA (US); Arjan Zoombelt, Philadelphia, PA (US)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/098,934

(22) PCT Filed: May 25, 2017

(86) PCT No.: PCT/US2017/034383
§ 371 (c)(1),
(2) Date: Nov. 5, 2018

(87) PCT Pub. No.: WO2017/205569
PCT Pub. Date: Nov. 30, 2017

(65) Prior Publication Data
US 2019/0097137 A1    Mar. 28, 2019

Related U.S. Application Data

(60) Provisional application No. 62/342,383, filed on May 27, 2016.

(51) Int. Cl.
*H01L 51/00* (2006.01)
*C08L 65/00* (2006.01)
(Continued)

(52) U.S. Cl.
CPC ........ *H01L 51/0036* (2013.01); *C07D 333/36* (2013.01); *C07D 495/14* (2013.01);
(Continued)

(58) Field of Classification Search
CPC .................................................. H01L 51/0036
See application file for complete search history.

(56) References Cited

U.S. PATENT DOCUMENTS

| | | | |
|---|---|---|---|
| 3,282,875 | A | 11/1966 | Connolly et al. |
| 4,358,545 | A | 11/1982 | Ezzell et al. |

(Continued)

FOREIGN PATENT DOCUMENTS

| | | |
|---|---|---|
| CN | 101720515 A | 6/2010 |
| CN | 103857724 A | 6/2014 |

(Continued)

OTHER PUBLICATIONS

Appleby AJ, Velev OA, LeHelloco JG, Parthasarthy A, Srinivasan S, DesMarteau DD, Gillette MS, Ghosh JK. Polymeric Perfluoro Bis-Sulfonimides as Possible Fuel Cell Electrolytes. Journal of the Electrochemical Society. Jan. 1, 1993;140(1):109-11.

(Continued)

*Primary Examiner* — William D Young
(74) *Attorney, Agent, or Firm* — Lerner, David, Littenberg, Krumholz & Mentlik, LLP

(57) ABSTRACT

Disclosed are electrically conductive polymer compositions, and their use in organic electronic devices. The electrically (Continued)

conductive polymer compositions include an intrinsically electrically conductive polymer having Formula II:

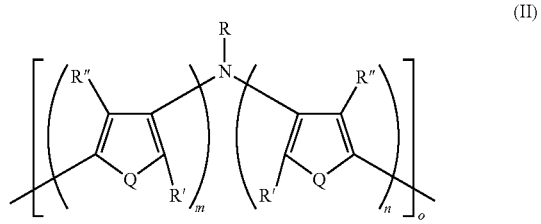

(II)

where Q, R, R', R", m, n, and o are defined in the present disclosure.

3 Claims, 2 Drawing Sheets

(51) Int. Cl.
| | |
|---|---|
| C08G 61/12 | (2006.01) |
| H01B 1/12 | (2006.01) |
| C08L 101/04 | (2006.01) |
| C07D 333/36 | (2006.01) |
| C07D 495/14 | (2006.01) |
| H01L 51/50 | (2006.01) |

(52) U.S. Cl.
CPC ............ *C08G 61/12* (2013.01); *C08G 61/124* (2013.01); *C08G 61/126* (2013.01); *C08L 65/00* (2013.01); *C08L 101/04* (2013.01); *H01B 1/127* (2013.01); *C08G 2261/11* (2013.01); *C08G 2261/124* (2013.01); *C08G 2261/148* (2013.01); *C08G 2261/1422* (2013.01); *C08G 2261/1424* (2013.01); *C08G 2261/1426* (2013.01); *C08G 2261/3162* (2013.01); *C08G 2261/3241* (2013.01); *C08G 2261/3243* (2013.01); *C08G 2261/334* (2013.01); *C08G 2261/44* (2013.01); *C08G 2261/512* (2013.01); *C08G 2261/95* (2013.01); *C08L 2203/20* (2013.01); *C08L 2205/03* (2013.01); *H01L 51/5088* (2013.01)

(56) References Cited

U.S. PATENT DOCUMENTS

| | | | |
|---|---|---|---|
| 4,433,082 | A | 2/1984 | Grot |
| 4,940,525 | A | 7/1990 | Ezzell et al. |
| 5,300,575 | A | 4/1994 | Jonas et al. |
| 5,463,005 | A | 10/1995 | Desmarteau |
| 6,150,426 | A | 11/2000 | Curtin et al. |
| 6,303,238 | B1 | 10/2001 | Thompson et al. |
| 6,670,645 | B2 | 12/2003 | Grushin et al. |
| 2002/0076576 | A1* | 6/2002 | Li ...................... H01L 51/0039 428/690 |
| 2004/0102577 | A1 | 5/2004 | Hsu et al. |
| 2005/0184287 | A1 | 8/2005 | Herron et al. |
| 2008/0286566 | A1 | 11/2008 | Prakash |
| 2010/0207109 | A1 | 8/2010 | Hsu et al. |
| 2011/0186827 | A1 | 8/2011 | Buennagel et al. |
| 2014/0235818 | A1* | 8/2014 | Schimperna ............ H01L 51/00 528/378 |
| 2015/0069302 | A1* | 3/2015 | Levi ........................ C08F 28/06 252/500 |

FOREIGN PATENT DOCUMENTS

| | | |
|---|---|---|
| EP | 1026152 A1 | 8/2000 |
| JP | 2006500463 A | 1/2006 |
| JP | 2011529975 A | 12/2011 |
| WO | 9831716 A1 | 7/1998 |
| WO | 9952954 A1 | 10/1999 |
| WO | 2000070655 A2 | 11/2000 |
| WO | 2001041512 A1 | 6/2001 |
| WO | 2003006537 A1 | 1/2003 |
| WO | 2003008424 A1 | 1/2003 |
| WO | 2003040257 A1 | 5/2003 |
| WO | 2003063555 A1 | 7/2003 |
| WO | 2003091688 A2 | 11/2003 |
| WO | 2004016710 A1 | 2/2004 |
| WO | 2005052027 A1 | 6/2005 |

OTHER PUBLICATIONS

DesMarteau DD. Novel perfluorinated ionomers and ionenes. Journal of fluorine chemistry. Jun. 1, 1995;72(2):203-8.

Feiring AE, Choi SK, Doyle M, Wonchoba ER. Novel aromatic polymers with pendant lithium periluoroalkylsulfonate or sulfonimide groups. Macromolecules. Dec. 12, 2000;33(25):9262-71.

Feiring AE, Wonchoba ER. Aromatic monomers with pendant fluoroalkylsulfonate and sulfonimide groups. Journal of Fluorine Chemistry. Jul. 1, 2000;105(1):129-35.

Gustafsson G, Cao Y, Treacy GM, Klavetter F, Colaneri N, Heeger AJ. Flexible light-emitting diodes made from soluble conducting polymers. Nature. Jun. 1992;357(6378):477.

Udum YA, Yildiz HB, Azak H, Sahin E, Talaz O, Çirpan A, Toppare L. Synthesis and spectroelectrochemistry of dithieno (3, 2-b: 2', 3'-d) pyrrole derivatives. Journal of Applied Polymer Science. Sep. 5, 2014;131(17).

Wong HL, Ko CC, Lam WH, Zhu N, Yam VW. Design and Synthesis of a New Class of Photochromic Diarylethene-Containing Dithieno [3, 2-b: 2', 3'-d] pyrroles and Their Switchable Luminescence Properties. Chemistry—A European Journal. Oct. 5, 2009;15(39):10005-9.

Yuen JD, Wang M, Fan J, Sheberla D, Kemei M, Banerji N, Scarongella M, Valouch S, Pho T, Kumar R, Chesnut EC. Importance of unpaired electrons in organic electronics. Journal of Polymer Science Part A: Polymer Chemistry. Jan. 15, 2015;53(2):287-93.

Zotti G, Berlin A, Zecchin S. Adsorption and electrochemical coupling of carboxyhexyl-substituted bi-and terthiophenes on ITO electrodes. Synthetic metals. May 1, 1999;101(1-3):622-3.

International Search Report including Written Opinion for PCT/US2017/034383 dated Sep. 7, 2017.

Chinese Search Report for Application No. 201780030468.7, dated Dec. 16, 2020, pp. 1-4.

Dai et al., Influence of the Terminal Electron Donor in D-D-π-A Organic Dye-Sensitized Solar Cells: Dithieno[3,2-b:2',3'-d]pyrrole versus Bis(amine), Applied Materials & Interfaces, Sep. 22, 2015, pp. 22436-22447, vol. 7, ACS Publications.

Outurquin et al., Synthesis of Dithieno[3,2-b:2',3'-e] pyridines and 4,8-Dihydrodithieno[3,2-b:2',3'-e]pyridines, Tetrahedron Letters, Sep. 1993, pp. 5719-5722, vol. 34, No. 36.

* cited by examiner

DIHETERO AMINES IN ELECTRICALLY CONDUCTIVE POLYMER COMPOSITIONS

CLAIM OF BENEFIT OF PRIOR APPLICATION

This application claims the benefit of U.S. Provisional Application No. 62/342,383, filed May 27, 2016, which is incorporated in its entirety herein by reference.

BACKGROUND INFORMATION

Field of the Disclosure

This disclosure relates in general to dihetero amine compounds, dihetero amine polymers, electrically conductive polymer compositions containing dihetero amine polymers, and the use of such materials in organic electronic devices.

Description of the Related Art

Organic electronic devices define a category of products that include an active layer. Such devices convert electrical energy into radiation, detect signals through electronic processes, convert radiation into electrical energy, or include one or more organic semiconductor layers.

Organic light-emitting diodes (OLEDs) are an organic electronic device comprising an organic layer capable of electroluminescence. OLEDs containing electrically conducting polymers can have the following configuration:

anode/buffer layer/EL material/cathode

The anode is typically any material that is transparent and has the ability to inject holes into the EL material, such as, for example, indium/tin oxide (ITO). The anode is optionally supported on a glass or plastic substrate. EL materials include fluorescent compounds, fluorescent and phosphorescent metal complexes, conjugated polymers, and mixtures thereof. The cathode is typically any material (such as, e.g., Ca or Ba) that has the ability to inject electrons into the EL material.

The buffer layer is typically an electrically conducting polymer and facilitates the injection of holes from the anode into the EL material layer. Typical electrically conducting polymers employed as buffer layers include polyaniline and polydioxythiophenes such as poly(3,4-ethylenedioxythiophene) (PEDOT). These materials can be prepared by polymerizing aniline or dioxythiophene monomers in aqueous solution in the presence of a water soluble polymeric acid, such as poly(styrenesulfonic acid) (PSS), as described in, for example, U.S. Pat. No. 5,300,575.

The aqueous electrically conductive polymer dispersions synthesized with water soluble polymeric sulfonic acids have undesirably-low pH levels. The low pH can contribute to decreased stress life of an EL device containing such a buffer layer, and contribute to corrosion within the device.

Electrically conducting polymers which have the ability to carry a high current when subjected to a low electrical voltage, also have utility as electrodes for electronic devices, such as thin film field effect transistors. In such transistors, an organic semiconducting film which has high mobility for electron and/or hole charge carriers, is present between source and drain electrodes. A gate electrode is on the opposite side of the semiconducting layer. To be useful for the electrode application, the electrically conducting polymers and the liquids for dispersing or dissolving the electrically conducting polymers have to be compatible with the semiconducting polymers and the solvents for the semiconducting polymers to avoid re-dissolution of either electrically conducting polymers or semiconducting polymers. Many electrically conductive polymers have conductivities which are too low for use as electrodes.

Thus, there is a continuing need for electrically conductive polymer compositions having improved physical and electrical properties.

SUMMARY

There is provided a compound having Formula I

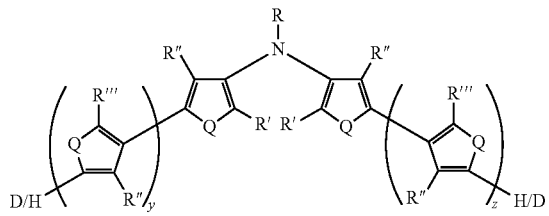

(I)

wherein:

Q is the same or different at each occurrence and is selected from the group consisting of S, P, Se, Te, O, P=O, and NR°;

R° is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R', R", and R''' are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof;

y is an integer from 0 to 4; and z is an integer from 0 to 4.

There is also provided a compound having Formula I'

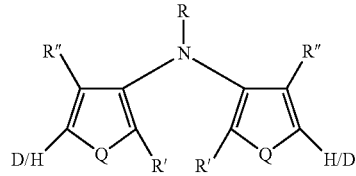

(I')

wherein:

Q is the same or different at each occurrence and is selected from the group consisting of S, P, Se, Te, O, P=O, and NR°;

R° is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R' and R" are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof.

There is also provided a polymer having Formula II

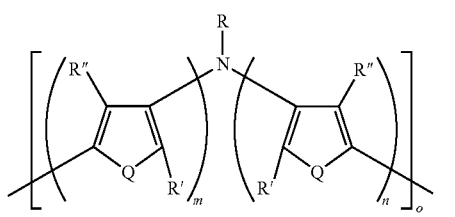

(II)

wherein:

Q is the same or different at each occurrence and is selected from the group consisting of S, P, Se, Te, O, P=O, and NR°;

R° is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R' and R" are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof;

m is an integer from 1-5;

n is an integer from 1-5; and o is an integer from 2-2000.

There is also provided an electrically conductive polymer composition comprising an intrinsically electrically conductive polymer doped with a non-fluorinated acid polymer, wherein the electrically conductive polymer has at least one monomeric unit derived from Formula II and having Formula II':

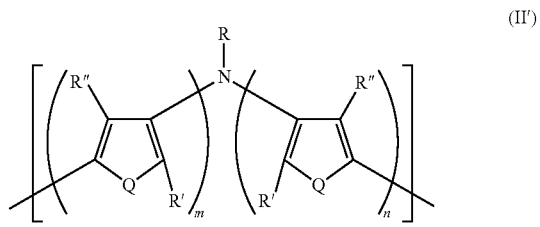

(II')

wherein:

Q is the same or different at each occurrence and is selected from the group consisting of S, PR°, Se, Te, O, P=O, and NR°;

R° is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R' and R" are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof;

m is an integer from 1-5; and n is an integer from 1-5.

In another embodiment, there is provided an electrically conductive polymer composition comprising an intrinsically electrically conductive polymer doped with a non-fluorinated acid polymer, wherein the electrically conductive polymer has at least one monomeric unit derived from Formula II.

In another embodiment, the composition further comprises a fluorinated acid polymer.

In another embodiment, there is provided an aqueous dispersion of the new electrically conductive polymer composition.

In another embodiment, there is provided a buffer layer comprising the new electrically conductive polymer composition.

In another embodiment, electronic devices comprising at least one layer comprising the new electrically conductive polymer composition are provided.

BRIEF DESCRIPTION OF THE DRAWINGS

Embodiments are illustrated in the accompanying figures to improve understanding of concepts as presented herein.

Figure 1:
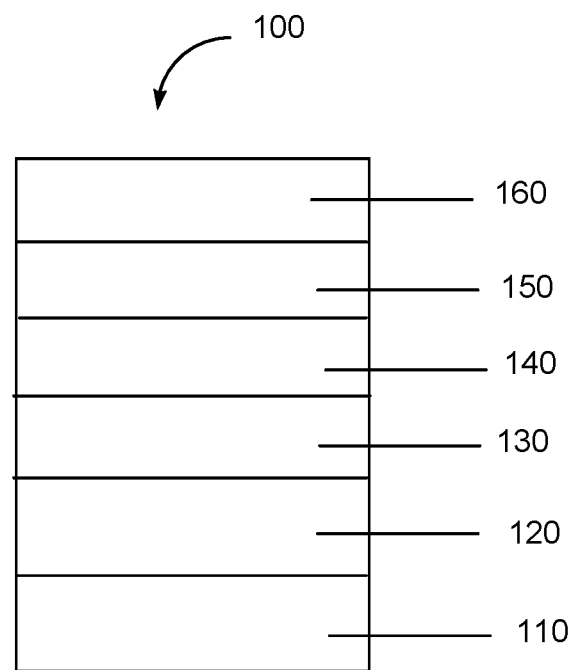
FIG. 1 includes an illustration of an exemplary organic device including a new compound or polymer described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Dihetero Amine Compounds having Formula I, the Dihetero Amine Polymers, the Non-Fluorinated Polymeric Acids, Preparation of the Doped Electrically Conductive Polymers, the Fluorinated Acid Polymers, Preparation of Composite Dispersions, Buffer Layers, Electronic Devices, and finally Examples.

1. Definitions and Clarification of Terms

Before addressing details of embodiments described below, some terms are defined or clarified.

As used in the "Definitions and Clarification of Terms", R, R', and R", and any other variables are generic designations and may be the same as or different from those defined in the formulas.

The term "acid polymer" is intended to mean a polymer having acidic groups.

The term "acid group" refers to a group capable of ionizing to donate a hydrogen ion to a Brønsted base.

The term "adjacent" as it refers to substituent groups refers to groups that are bonded to carbons that are joined together with a single or multiple bond. Exemplary adjacent R groups are shown below:

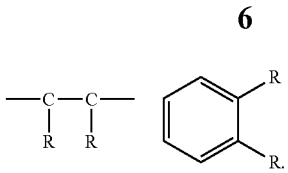

The term "alcohol" as it refers to a substituent group, is intended to mean the group HOR—, where R is an alkyl group.

The term "alkenyl" refers to a group derived from an aliphatic hydrocarbon having at least one carbon-carbon double bond; and includes linear, branched, and cyclic groups which may be substituted or unsubstituted. The term "heteroalkenyl" is intended to mean an alkenyl group wherein one or more of the carbon atoms within the alkenyl group has been replaced by another atom; such as nitrogen, oxygen, sulfur, and the like. The term "alkenylene" refers to an alkenyl group having two points of attachment.

The term "alkyl" is intended to mean a group derived from an aliphatic hydrocarbon and includes a linear, branched, or a cyclic group. A group "derived from" a compound, indicates the radical formed by removal of one H or D. In some embodiments, an alkyl has from 1-20 carbon atoms.

The term "alkoxy" is intended to mean the group RO—, where R is an alkyl group.

The term "alkylseleno" is intended to mean the group RSe—, where R is an alkyl group.

The term "alkylsilyl" is intended to mean the group RSi—, where R is an alkyl group.

The term "alkthio" is intended to mean the group RS—, where R is an alkyl group.

The term "aqueous" refers to a liquid that has a significant portion of water, and in one embodiment it is at least about 40% by weight water, in some embodiments, at least about 60% by weight water.

The term "aromatic compound" is intended to mean an organic compound comprising at least one unsaturated cyclic group having 4n+2 delocalized pi electrons.

The term "aryl" is intended to mean a group derived from an aromatic hydrocarbon having one point of attachment. The term includes groups which have a single ring and those which have multiple rings which can be joined by a single bond or fused together. Hydrocarbon aryl groups have only carbon in the ring structures. Heteroaryl groups have at least one heteroatom in a ring structure. An N-heteroaryl group has at least one nitrogen in a ring structure. The term "alkylaryl" is intended to mean an aryl group having one or more alkyl substituents.

The term "aryloxy" is intended to mean the group RO—, where R is an aryl group.

The term "branched alkyl" is intended to mean a group derived from an aliphatic hydrocarbon that has at least one secondary or tertiary carbon as the point of attachment. A secondary alkyl group has the structure:

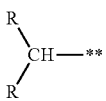

where the R groups are the same or different and are alkyl groups and ** represents the point of attachment. A tertiary alkyl group has the structure:

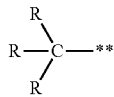

where the R groups are the same or different and are alkyl groups and ** represents the point of attachment. Additional branching may be present in one or more of the R groups.

The term "buffer layer" or "buffer material" is intended to refer to electrically conductive or semiconductive layers or materials which may have one or more functions in an organic electronic device, including but not limited to, planarization of the underlying layer, charge transport and/or charge injection properties, scavenging of impurities such as oxygen or metal ions, and other aspects to facilitate or to improve the performance of an organic electronic device.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage. The symbol "H/D" or "D/H" indicates that the substituent can be either H or D.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "doped" as it refers to an electrically conductive polymer, is intended to mean that the electrically conductive polymer has a polymeric counterion to balance the charge on the electrically conductive polymer.

The term "doped conductive polymer" is intended to mean the electrically conductive polymer and the polymeric counterion that is associated with it.

The term "electrically conducting" or "electrically conductive" as it refers to a material, is intended to mean a material which is inherently or intrinsically capable of electrical conductivity without the addition of carbon black or conductive metal particles.

The term "ether" as it refers to a substituent group is intended to mean the group R'OR—, where R and R' are the same or different and are an alkyl or aryl group. A "polyether" is intended to mean the group R'(OR')$_x$OR—, where R' is the same or different at each occurrence and x is in integer of 1 or more.

The term "fluorinated acid polymer" refers to a polymer having groups with acidic protons, and where at least one of the hydrogens bonded to carbon in the polymer has been replaced by fluorine.

The terms "fully-fluorinated" and "perfluorinated" are used interchangeably and refer to a compound where all of the available hydrogens bonded to carbon have been replaced by fluorine.

The term "germyl" refers to the group R$_3$Ge—, where R is the same or different at each occurrence and is H, D, C1-20 alkyl, deuterated alkyl, fluoroalkyl, aryl, or deuterated aryl.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell).

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "polymer" refers to a polymer or oligomer having at least 2 repeat units. The term includes homopolymers having only one kind, or species, of monomeric unit, and copolymers having two or more different monomeric units, including copolymers formed from monomeric units of different species. The term "intrinsically conductive" refers to a material which is capable of electrical conductivity without the addition of carbon black or conductive metal particles.

The term "silyl" refers to the group R$_3$Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The terms "terminate," "terminal," or "terminated" refer to functional groups beyond which a carbon chain does not extend.

All groups may be unsubstituted or substituted. The substituent groups are discussed below. In a structure where a substituent bond passes through one or more rings as shown below,

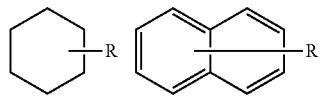

it is meant that the substituent R may be bonded at any available position on the one or more rings.

A "non-H/D group" is any substituent group that is not a single H or D.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Dihetero Amine Compounds having Formula I

The new dihetero amine compounds described herein have Formula I

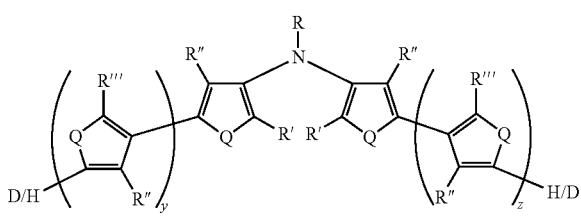

wherein:

Q is the same or different at each occurrence and is selected from the group consisting of S, PR$^\circ$, Se, Te, O, P=O, and NR$^\circ$;

R$^\circ$ is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R', R", and R''' are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof;

y is an integer from 0 to 4; and z is an integer from 0 to 4.

In some embodiments of Formula I, the compound is deuterated.

In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, Q=S.
In some embodiments of Formula I, Q=PR$^\circ$.
In some embodiments of Formula I, Q=Se.
In some embodiments of Formula I, Q=Te.
In some embodiments of Formula I, Q=O.
In some embodiments of Formula I, Q=P=O.

In some embodiments of Formula I, Q=NR° and R° is selected from the group consisting of H and D.

In some embodiments of Formula I, Q=NR° and R° is selected from the group consisting of alkyl and deuterated alkyl.

In some embodiments of Formula I, Q=NR° and R° is selected from the group consisting of aryl and deuterated aryl.

In some embodiments of Formula I, all the Q's are the same.

In some embodiments of Formula I, the Q's are different from one another.

In some embodiments of Formula I, R is selected from the group consisting of H and D.

In some embodiments of Formula I, R is selected from the group consisting of alkyl, alkoxy, fluoroalkyl, deuterated alkyl, deuterated partially-fluorinated alkyl, and deuterated alkoxy.

In some embodiments of Formula I, R is selected from the group consisting of aryl, aryloxy, heteroaryl, deuterated aryl, deuterated aryloxy, and deuterated heteroaryl.

In some embodiments of Formula I, R is selected from the group consisting of silyl, siloxane, siloxy, deuterated silyl, deuterated siloxane, and deuterated siloxy.

In some embodiments of Formula I, R is selected from the group consisting of germyl and deuterated germyl.

In some embodiments of Formula I, R is a non-H/D group that is terminated by an hydroxyl.

In some embodiments of Formula I, R is a non-H/D group that is terminated by an ether.

In some embodiments of Formula I, R is a non-H/D group that is terminated by an alkoxy group.

In some embodiments of Formula I, R is a non-H/D group that is terminated by an alcohol.

In some embodiments of Formula I, R is a non-H/D group that is terminated by an amine.

In some embodiments of Formula I, R is a non-H/D group that is terminated by an amide.

In some embodiments of Formula I, R is a non-H/D group that is terminated by an ester.

In some embodiments of Formula I, R is a non-H/D group that is terminated by a carboxylic acid.

In some embodiments of Formula I, R is a non-H/D group that is terminated by a sulfonic acid.

In some embodiments of Formula I, R is a non-H/D group that is terminated by a phosphate.

In some embodiments of Formula I, R' and R" are the same or different and are selected from the group consisting of H and D.

In some embodiments of Formula I, R' is selected from the group consisting of H and D.

In some embodiments of Formula I, R' is selected from the group consisting of alkyl having 1-8 carbon atoms and deuterated analogs thereof.

In some embodiments of Formula I, R' and R" are the same or different and are selected from the group consisting of alkyl, alkoxy, fluoroalkyl, deuterated alkyl, deuterated partially-fluorinated alkyl, and deuterated alkoxy.

In some embodiments of Formula I, R' and R" are the same or different and are selected from the group consisting of aryl, aryloxy, heteroaryl, deuterated aryl, deuterated aryloxy, and deuterated heteroaryl.

In some embodiments of Formula I, R' and R" are the same or different and are selected from the group consisting of silyl, siloxane, siloxy, deuterated silyl, deuterated siloxane, and deuterated siloxy.

In some embodiments of Formula I, R' and R" are the same or different and are selected from the group consisting of germyl and deuterated germyl.

In some embodiments of Formula I, R' and R" are the same or different and are non-H/D groups that are terminated by an hydroxyl.

In some embodiments of Formula I, R' and R" are the same or different and are non-H/D groups that are terminated by an ether.

In some embodiments of Formula I, R' and R" are the same or different and are non-H/D groups that are terminated by an alkoxy group.

In some embodiments of Formula I, R' and R" are the same or different and are non-H/D groups that are terminated by an alcohol.

In some embodiments of Formula I, R' and R" are the same or different and are non-H/D groups that are terminated by an amine.

In some embodiments of Formula I, R' and R" are the same or different and are non-H/D groups that are terminated by an amide.

In some embodiments of Formula I, R' and R" are the same or different and are non-H/D groups that are terminated by an ester.

In some embodiments of Formula I, R' and R" are the same or different and are non-H/D groups that are terminated by a carboxylic acid.

In some embodiments of Formula I, R' and R" are the same or different and are non-H/D groups that are terminated by a sulfonic acid.

In some embodiments of Formula I, R' and R" are the same or different and are non-H/D groups that are terminated by a phosphate. In some embodiments of Formula I, R" is H or D.

In some embodiments of Formula I, R" is selected from the group consisting of alkyl, alkoxy, fluoroalkyl, deuterated alkyl, deuterated partially-fluorinated alkyl, and deuterated alkoxy.

In some embodiments of Formula I, R" is selected from the group consisting of aryl, aryloxy, heteroaryl, deuterated aryl, deuterated aryloxy, and deuterated heteroaryl.

In some embodiments of Formula I, R" is selected from the group consisting of silyl, siloxane, siloxy, deuterated silyl, deuterated siloxane, and deuterated siloxy.

In some embodiments of Formula I, R" is selected from the group consisting of germyl and deuterated germyl.

In some embodiments of Formula I, R" is a non-H/D group that is terminated by an hydroxyl.

In some embodiments of Formula I, R" is a non-H/D group that is terminated by an alkoxy group.

In some embodiments of Formula I, R" is a non-H/D group that is terminated by an ether.

In some embodiments of Formula I, R" is a non-H/D group that is terminated by an alcohol.

In some embodiments of Formula I, R" is a non-H/D group that is terminated by an amine.

In some embodiments of Formula I, R" is a non-H/D group that is terminated by an amide.

In some embodiments of Formula I, R" is a non-H/D group that is terminated by an ester.

In some embodiments of Formula I, R" is a non-H/D group that is terminated by a carboxylic acid.

In some embodiments of Formula I, R" is a non-H/D group that is terminated by a sulfonic acid.

In some embodiments of Formula I, R" is a non-H/D group that is terminated by a phosphate.

In some embodiments of Formula I, R'" is H or D.

In some embodiments of Formula I, R''' is selected from the group consisting of alkyl, alkoxy, fluoroalkyl, deuterated alkyl, deuterated partially-fluorinated alkyl, and deuterated alkoxy.

In some embodiments of Formula I, R''' is selected from the group consisting of aryl, aryloxy, heteroaryl, deuterated aryl, deuterated aryloxy, and deuterated heteroaryl.

In some embodiments of Formula I, R''' is selected from the group consisting of silyl, siloxane, siloxy, deuterated silyl, deuterated siloxane, and deuterated siloxy.

In some embodiments of Formula I, R''' is selected from the group consisting of germyl and deuterated germyl.

In some embodiments of Formula I, R''' is a non-H/D group that is terminated by an hydroxyl.

In some embodiments of Formula I, R''' is a non-H/D group that is terminated by an alkoxy group.

In some embodiments of Formula I, R''' is a non-H/D group that is terminated by an ether. In some embodiments of Formula I, R''' is a non-H/D group that is terminated by an alcohol.

In some embodiments of Formula I, R''' is a non-H/D group that is terminated by an amine.

In some embodiments of Formula I, R''' is a non-H/D group that is terminated by an amide.

In some embodiments of Formula I, R''' is a non-H/D group that is terminated by an ester.

In some embodiments of Formula I, R''' is a non-H/D group that is terminated by a carboxylic acid.

In some embodiments of Formula I, R''' is a non-H/D group that is terminated by a sulfonic acid.

In some embodiments of Formula I, R''' is a non-H/D group that is terminated by a phosphate.

In some embodiments of Formula I, there are no carbazolyl groups.

In some embodiments of Formula I, y=0.
In some embodiments of Formula I, y=1.
In some embodiments of Formula I, y=2.
In some embodiments of Formula I, y=3.
In some embodiments of Formula I, y=4.
In some embodiments of Formula I, z=0.
In some embodiments of Formula I, z=1.
In some embodiments of Formula I, z=2.
In some embodiments of Formula I, z=3.
In some embodiments of Formula I, z=4.
In some embodiments of Formula I, y+z=1.

In some embodiments of Formula I, the R' groups together represent a single bond which forms a fused ring and the compound has Formula I-a (I-a)

where Q, R, R", R''', y, and z are as defined in Formula I. All of the above-described embodiments for Q, R, R", R''', y, and z in Formula I apply equally to Formula I-a.

In some embodiments of Formula I, y=z=0 and the compound has Formula I'

(I')

where Q, R, R', and R" are as defined in Formula I. All of the above-described embodiments for Q, R, R', and R" in Formula I apply equally to Formula I'.

In some embodiments of Formula I, y=z=0 and the R' groups together represent a single bond which forms a fused ring, and the compound has Formula I'-a (I'-a)

where Q, R, and R" are as defined in Formula I. All of the above-described embodiments for Q, R, and R" in Formula I apply equally to Formula I'-a.

Any of the above embodiments for Formula I, Formula I-a, Formula I', and Formula I'-a can be combined with one or more of the other embodiments, so long as they are not mutually exclusive. For example, the embodiment in which Q is S can be combined with the embodiment in which R is an alkyl group terminated by a carboxylic acid and R'=R"=aryl. The same is true for the other non-mutually-exclusive embodiments discussed above. The skilled person would understand which embodiments were mutually exclusive and would thus readily be able to determine the combinations of embodiments that are contemplated by the present application.

The compounds of Formula I can be made using transition metal catalyzed C—N formation routes by coupling of halide-containing thiophenes and a primary amine. Examples of synthetic routes are shown below:

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

Additional exemplary preparations are given in the Examples.

Some non-limiting examples of compounds having Formula I are shown below.

Compound I-1

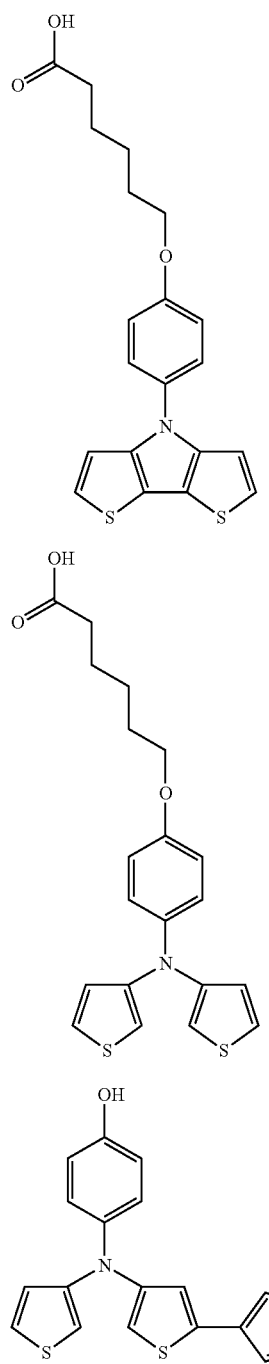

Compound I-2

Compound I-3

Compound I-4

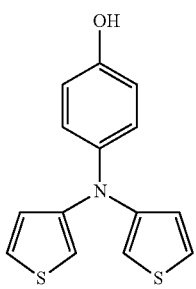

Compound I-5

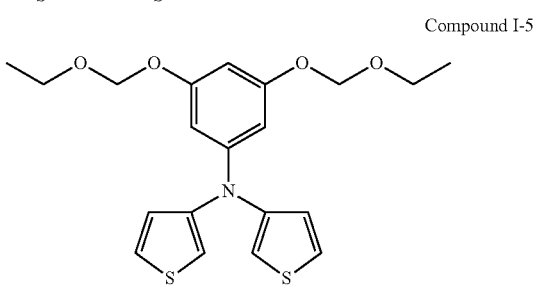

Compound I-6

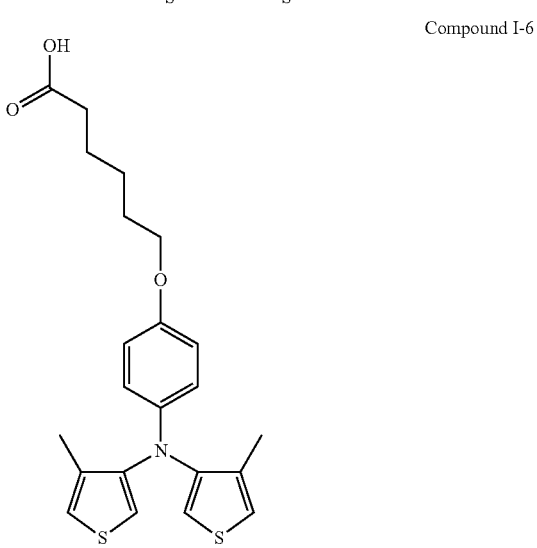

Compound I-7

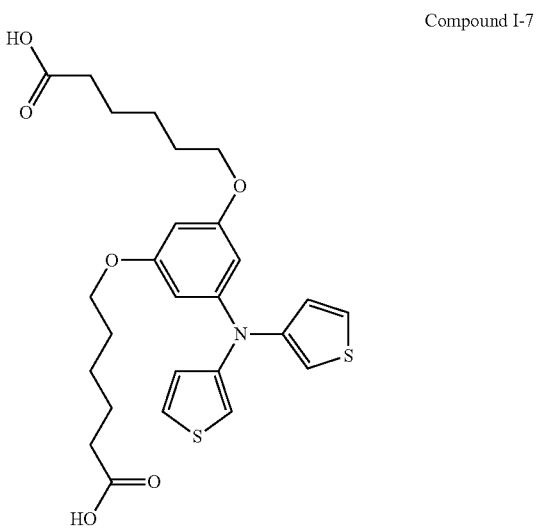

Compound I-8
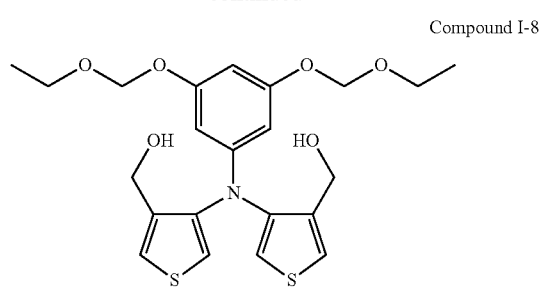
Compound I-9
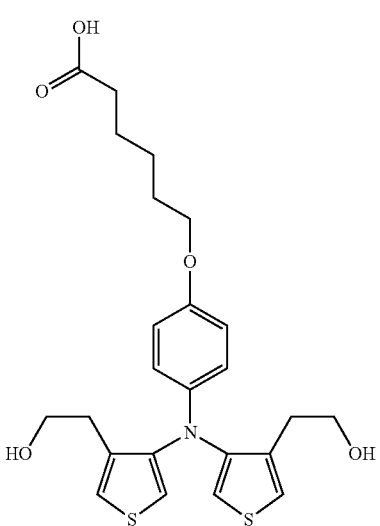
Compound I-10
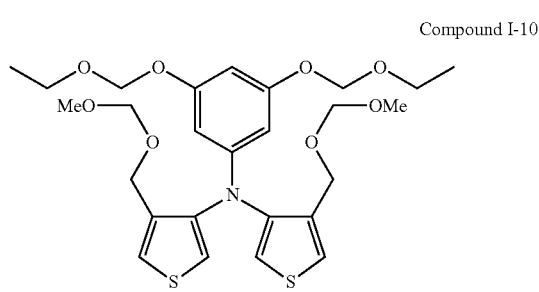
Compound I-11
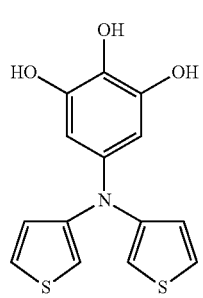
Compound I-12
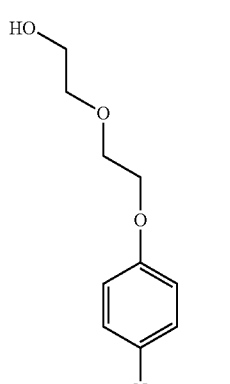
Compound I-13
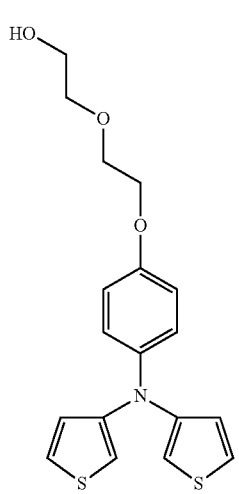
Compound I-14
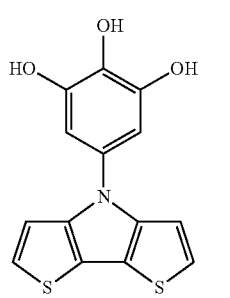
3. Dihetero Amine Polymers
In some embodiments, the new dihetero amine polymers described herein have Formula II
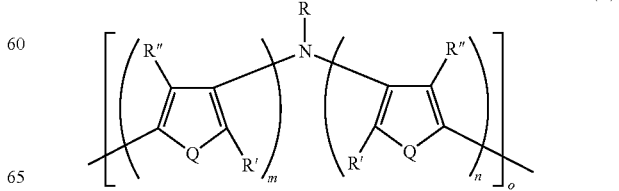
(II)

wherein:

Q is the same or different at each occurrence and is selected from the group consisting of S, PR°, Se, Te, O, P=O, and NR°;

R° is the same or different at each occurrence and is selected from the group consisting of H, D, alkyl, deuterated alkyl, aryl, and deuterated aryl;

R is selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; with the proviso that when R is any non-H/D group it is terminated by a functional group selected from the group consisting of hydroxyl, alcohol, alkoxy, ether, amine, amide, ester, carboxylic acid, sulfonic acid, phosphate, and deuterated analogs thereof;

R' and R" are the same or different at each occurrence and are selected from the group consisting of H, D, alkyl, alkoxy, ether, polyether, fluoroalkyl, aryl, aryloxy, heteroaryl, silyl, siloxane, siloxy, germyl, deuterated alkyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl; wherein two R' groups can together represent a single bond which forms a fused ring; with the proviso that any non-H/D group may be terminated by a functional group selected from the group consisting of hydroxyl, alcohol, alkoxy, ether, amine, amide, ester, carboxylic acid, sulfonic acid, phosphate, and deuterated analogs thereof;

m is an integer from 1-5;

n is an integer from 1-5; and o is an integer from 2-2000.

As used herein, the term "dihetero amine polymers having Formula II" is intended to designate a compound based on a repeat unit, or monomer, as defined by Formula II. The amino nitrogen in such polymers, when not substituted such that R=H or D, is substituted with an R that is terminated by a functional group selected from the group consisting of hydroxyl, alcohol, alkoxy, ether, amine, amide, ester, carboxylic acid, sulfonic acid, and phosphate. The presence of such terminal functional groups, in combination with the variable possibilities for the remainder of the R groups, affords the dihetero amine polymers having Formula II a variability in water solubility that can be optimized for preparation of buffer layers that exhibit optimum physical and electronic properties under a variety of conditions. Further, buffer layers constructed based on dihetero amine polymers having Formula II exhibit greater stability with respect to oxygen compared to other buffer layers.

All embodiments identified for Q, R, R', and R" of Formula I in section 2 above apply equally to the same units in Formula II.

Also, in some embodiments of Formula II, m=1.
In some embodiments of Formula II, m=2.
In some embodiments of Formula II, m=3.
In some embodiments of Formula II, m=4.
In some embodiments of Formula II, m=5.
In some embodiments of Formula II, n=1.
In some embodiments of Formula II, n=2.
In some embodiments of Formula II, n=3.
In some embodiments of Formula II, n=4.
In some embodiments of Formula II, n=5.
In some embodiments of Formula II, o=2.
In some embodiments of Formula II, o=3-5.
In some embodiments of Formula II, o=6-10.
In some embodiments of Formula II, o>10.
In some embodiments of Formula II, o=10-2000.
In some embodiments of Formula II, o>100.
In some embodiments of Formula II, o=100-2000.
In some embodiments of Formula II, o=1000-2000.
In some embodiments of Formula II, there are no carbazolyl groups.

In some embodiments of Formula II, the R' groups together represent a single bond which forms a fused ring and the polymer has Formula II-a

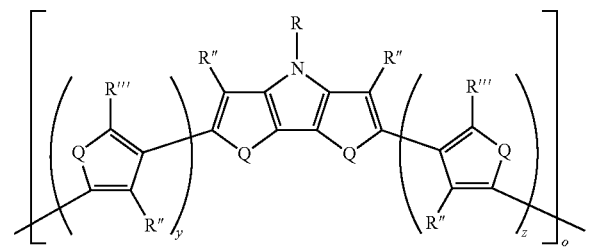

(II-a)

where o is as defined in Formula II and Q, R, R", R''', y, and z are as defined in Formula I. All of the above-described embodiments for o in Formula II and for Q, R, R", R''', y, and z in Formula I apply equally to Formula II-a.

In some embodiments of Formula II, the polymer is a homopolymer.

In some embodiments of Formula II-a, the polymer is a homopolymer.

In some embodiments, the dihetero amine polymer is a copolymer having at least one monomeric unit derived from Formula II and having Formula II'

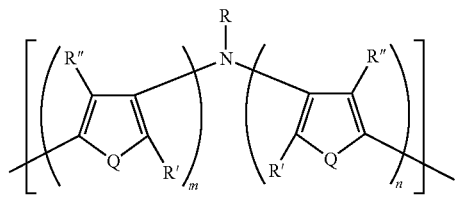

(II')

where Q, R, R', R", m, and n are as defined in Formula II. All of the above-described embodiments for Q, R, R', R", m and n in Formula II apply equally to Formula II'.

In some embodiments of Formula II, the R' groups together represent a single bond which forms a fused ring and the polymer has Formula II'-a

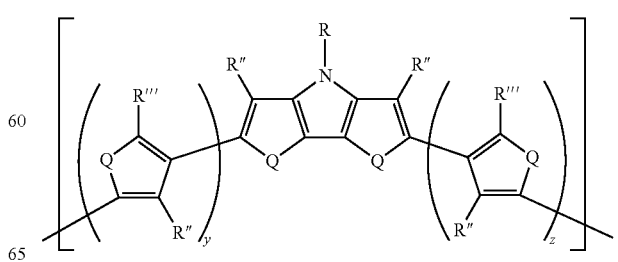

(II'-a)

where Q, R, R", R''', y, and z are as defined in Formula II-a.

All of the above-described embodiments for Q, R, R", R''', y, and z in Formula II-a apply equally to Formula II-a.

The exact composition of one or more comonomers will depend on the desired properties and intended use of the dihetero amine copolymer. In some embodiments, suitable comonomers are derived from hydrocarbon aromatic compounds and heteroaromatic compounds. Exemplary monomers include, but are not limited to, monomers derived from the group consisting of naphthalene, anthracene, fluorene, phenanthrene, triphenylene, thiophene, benzothiophene, pyrrole, carbazole, triarylamines, substituted derivatives thereof, and deuterated analogs thereof.

Any of the above embodiments for Formula II or Formula II-a can be combined with one or more of the other embodiments, so long as they are not mutually exclusive. For example, the embodiment in which Q is S can be combined with the embodiment in which R is an alkyl group terminated by a carboxylic acid and m=n=1. The same is true for the other non-mutually-exclusive embodiments discussed above. The skilled person would understand which embodiments were mutually exclusive and would thus readily be able to determine the combinations of embodiments that are contemplated by the present application.

Similarly, any of the above embodiments for Formula II' or Formula II'-a can be combined with one or more of the other embodiments, so long as they are not mutually exclusive.

The polymers of Formula II can be prepared as illustrated for the case of Polymer II-1 (below):

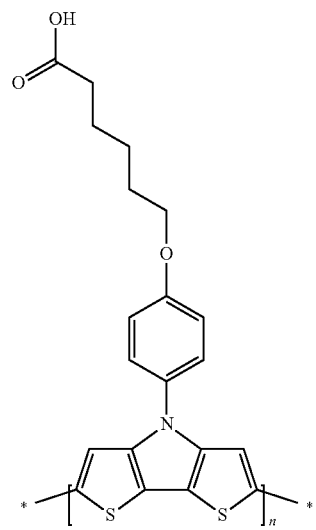

Deuterated polymers can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

Additional exemplary preparations are given in the Examples.

Some non-limiting examples of polymers having Formula II are shown below.

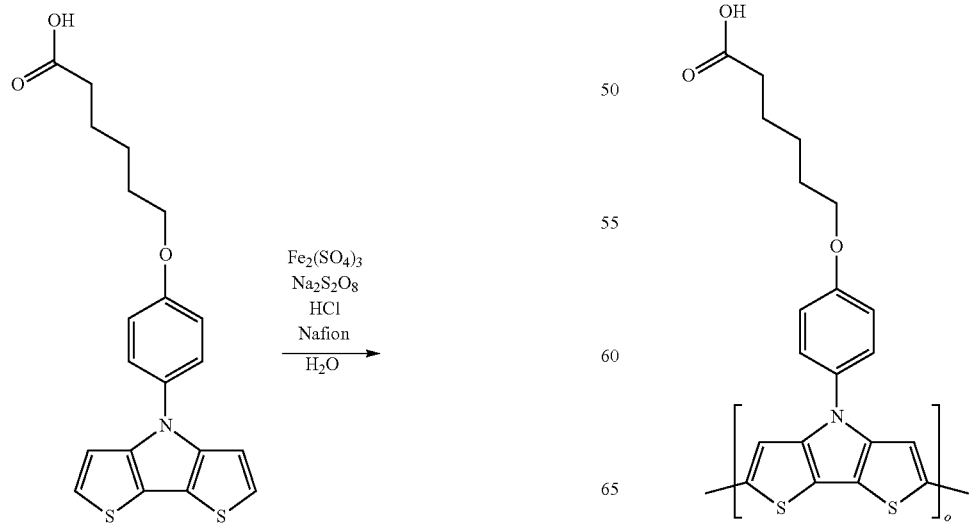

Polymer II-2

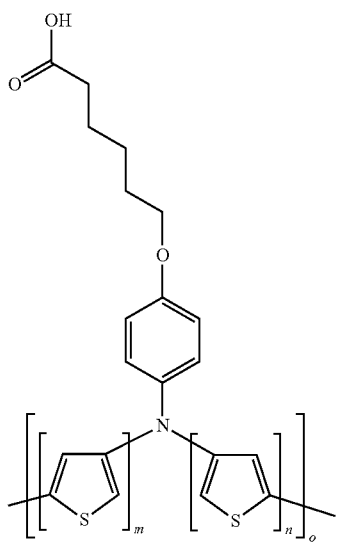

Polymer II-3

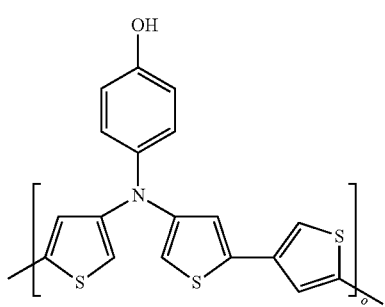

Polymer II-4

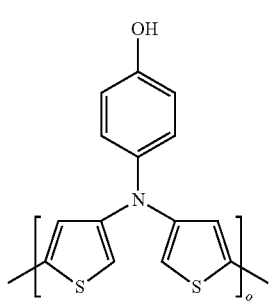

Polymer II-5

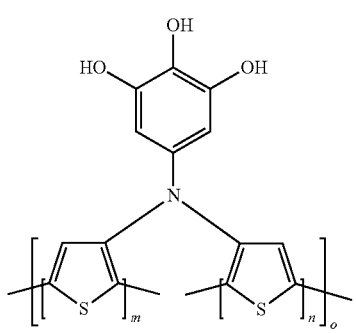

Polymer II-6

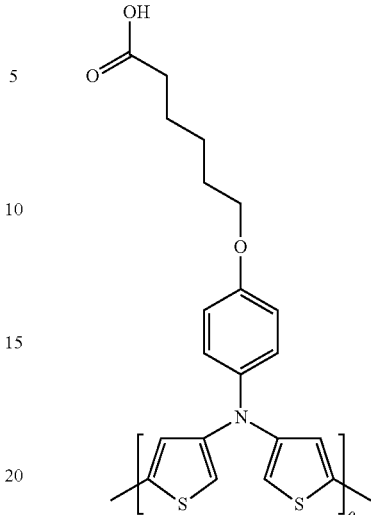

In some embodiments of Polymer II-2, m=n=1.
In some embodiments of Polymer II-5, m=n=1.

4. Non-Fluorinated Polymeric Acids

Any non-fluorinated polymeric acid which is capable of doping the polymer having Formula II can be used.

The use of such acids with electrically conducting polymers such as polythiophenes, polyanilines and polypyrroles is well known in the art. Examples of acidic groups include, but are not limited to, carboxylic acid groups, sulfonic acid groups, sulfonimide groups, phosphoric acid groups, phosphonic acid groups, and combinations thereof. The acidic groups can all be the same, or the polymer may have more than one type of acidic group.

In one embodiment, the acid is a non-fluorinated polymeric sulfonic acid. Some non-limiting examples of the acids are poly(styrenesulfonic acid) ("PSSA"), poly(2-acrylamido-2-methyl-1-propanesulfonic acid) ("PAAMPSA"), and mixtures thereof.

The amount of non-fluorinated polymeric acid present is generally in excess of that required to counterbalance the charge on the electrically conducting polymer. In some embodiments, the ratio of acid equivalents of non-fluorinated polymeric acid to molar equivalents of electrically conducting polymer is in the range of 1-5.

5. Preparation of the Doped Electrically Conductive Polymer

The new electrically conductive polymer composition is prepared by chemical polymerization of the precursor dihetero amine compounds in the presence of the non-fluorinated acid polymer to form a dispersion. Optionally, the pH of the dispersion can be adjusted.

Alternatively, films of the electrically conductive polymer on a substrate can be formed by electrochemical polymerization of the precursor monomers in the presence of the non-fluorinated acid polymer.

(i) Chemical Polymerization

In one embodiment, the electrically conductive polymer composition is formed by the oxidative polymerization of the precursor dihetero amine compounds in the presence of the non-fluorinated acid polymer. In one embodiment, the precursor dihetero amine compounds comprise one type of conductive precursor monomer. In one embodiment, the dihetero amine compounds comprise two or more different conductive precursor monomers. In one embodiment, the dihetero amine compounds comprise an intermediate precursor monomer having the structure A-B-C, where A and C represent dihetero amine compounds, which can be the same or different, and B represents a non-conductive precursor monomer. In one embodiment, the intermediate precursor monomer is polymerized with one or more conductive precursor monomers.

In one embodiment, the oxidative polymerization is carried out in a homogeneous aqueous solution. In another embodiment, the oxidative polymerization is carried out in an emulsion of water and an organic solvent. In general, some water is present in order to obtain adequate solubility of the oxidizing agent and/or catalyst. Oxidizing agents such as ammonium persulfate, sodium persulfate, potassium persulfate, and the like, can be used. A catalyst, such as ferric chloride, or ferric sulfate may also be present. The resulting polymerized product will be a solution, dispersion, or emulsion of the electrically conductive polymer doped with the fluorinated acid polymer. In one embodiment, the electrically conductive polymer is positively charged, and the charges are balanced by the non-fluorinated acid polymer anion.

In one embodiment, the polymerization is carried out in the presence of co-dispersing liquids which are miscible with water. Examples of suitable co-dispersing liquids include, but are not limited to ethers, alcohols, alcohol ethers, cyclic ethers, ketones, nitriles, sulfoxides, amides, and combinations thereof. In one embodiment, the co-dispersing liquid is an alcohol. In one embodiment, the co-dispersing liquid is an organic solvent selected from n-propanol, isopropanol, t-butanol, dimethylacetamide, dimethylformamide, N-methylpyrrolidone, and mixtures thereof. In general, the amount of co-dispersing liquid should be less than about 60% by volume. In one embodiment, the amount of co-dispersing liquid is less than about 30% by volume. In one embodiment, the amount of co-dispersing liquid is between 5 and 50% by volume. The use of a co-dispersing liquid in the polymerization significantly reduces particle size and improves filterability of the dispersions. In addition, buffer materials obtained by this process show an increased viscosity and films prepared from these dispersions are of high quality.

The co-dispersing liquid can be added to the reaction mixture at any point in the process.

In one embodiment, the polymerization is carried out in the presence of a co-acid which is a Brønsted acid. The acid can be an inorganic acid, such as HCl, sulfuric acid, and the like, or an organic acid, such as acetic acid or p-toluenesulfonic acid. Alternatively, the acid can be a water soluble polymeric acid such as poly(styrenesulfonic acid), poly(2-acrylamido-2-methyl-1-propanesulfonic acid, or the like, or a second fluorinated acid polymer, as described above. Combinations of acids can be used.

The co-acid can be added to the reaction mixture at any point in the process prior to the addition of either the oxidizer or the precursor monomer, whichever is added last. In one embodiment, the co-acid is added before both the precursor monomers and the non-fluorinated acid polymer, and the oxidizer is added last. In one embodiment the co-acid is added prior to the addition of the precursor monomers, followed by the addition of the non-fluorinated acid polymer, and the oxidizer is added last.

In one embodiment, the polymerization is carried out in the presence of both a co-dispersing liquid and a co-acid.

In one embodiment, a reaction vessel is charged first with a mixture of water, alcohol co-dispersing agent, and inorganic co-acid. To this is added, in order, the precursor monomers, an aqueous solution or dispersion of non-fluorinated acid polymer, and an oxidizer. The oxidizer is added slowly and dropwise to prevent the formation of localized areas of high ion concentration which can destabilize the mixture. In another embodiment, the oxidizer and precursor monomers are injected into the reaction mixture separately and simultaneously at a controlled rate. The mixture is stirred and the reaction is then allowed to proceed at a controlled temperature. When polymerization is completed, the reaction mixture is treated with a strong acid cation resin, stirred and filtered; and then treated with a base anion exchange resin, stirred and filtered. Alternative orders of addition can be used, as discussed above.

In the method of making the electrically conductive polymer, the molar ratio of oxidizer to total precursor monomer is generally in the range of 0.1 to 2.0; and in one embodiment is 0.4 to 1.5. The molar ratio of non-fluorinated acid polymer to total precursor monomer is generally in the range of 0.2 to 5. In one embodiment, the ratio is in the range of 1 to 4. The overall solid content is generally in the range of about 1.0% to 10% in weight percentage; and in one embodiment of about 2% to 4.5%. The reaction temperature is generally in the range of about 4° C. to 50° C.; in one embodiment about 20° C. to 35° C. The molar ratio of optional co-acid to precursor monomer is about 0.05 to 4. The addition time of the oxidizer may influence particle size and viscosity. In some embodiments, the particle size can be reduced by slowing down the addition speed. In parallel, the viscosity is also reduced by slowing down the addition speed.

In some embodiments, the reaction time is in the range of about 10 minutes to about 30 hours.

(ii) pH Adjustment

As synthesized, the aqueous dispersions of the doped conductive polymer generally have a very low pH. In one embodiment, the pH is adjusted to higher values, without adversely affecting the properties in devices. In one embodiment, the pH of the dispersion is adjusted to about 1.5 to about 4. In one embodiment, the pH is adjusted to between 3 and 4. It has been found that the pH can be adjusted using known techniques, for example, ion exchange or by titration with an aqueous basic solution.

In one embodiment, after completion of the polymerization reaction, the as-synthesized aqueous dispersion is contacted with at least one ion exchange resin under conditions suitable to remove decomposed species, side reaction products, and unreacted monomers, and to adjust pH, thus producing a stable, aqueous dispersion with a desired pH. In one embodiment, the as-synthesized aqueous dispersion is contacted with a first ion exchange resin and a second ion exchange resin, in any order. The as-synthesized aqueous dispersion can be treated with both the first and second ion exchange resins simultaneously, or it can be treated sequentially with one and then the other.

Ion exchange is a reversible chemical reaction wherein an ion in a fluid medium (such as an aqueous dispersion) is exchanged for a similarly charged ion attached to an immobile solid particle that is insoluble in the fluid medium. The term "ion exchange resin" is used herein to refer to all such substances. The resin is rendered insoluble due to the crosslinked nature of the polymeric support to which the ion exchanging groups are attached. Ion exchange resins are classified as cation exchangers or anion exchangers. Cation exchangers have positively charged mobile ions available for exchange, typically protons or metal ions such as sodium ions. Anion exchangers have exchangeable ions which are negatively charged, typically hydroxide ions. In some embodiments, weak base ion-exchange resins can be used.

In one embodiment, the first ion exchange resin is a cation, acid exchange resin, which can be in protonic form. The second ion exchange resin is a basic, anion exchange resin. In one embodiment, the first ion exchange resin is a basic, anion exchange resin and the second ion exchange resin is a cation, acid exchange resin, which can be in protonic or metal ion, typically sodium ion, form.

Both acidic, cation including proton exchange resins and basic, anion exchange resins are contemplated for use in the practice of the invention. In one embodiment, the acidic, cation exchange resin is an inorganic acid, cation exchange resin, such as a sulfonic acid cation exchange resin. Sulfonic acid cation exchange resins contemplated for use in the practice of the invention include, for example, sulfonated styrene-divinylbenzene copolymers, sulfonated crosslinked styrene polymers, phenol-formaldehyde-sulfonic acid resins, benzene-formaldehyde-sulfonic acid resins, and mixtures thereof. In another embodiment, the acidic, cation exchange resin is an organic acid, cation exchange resin, such as carboxylic acid, acrylic or phosphorous cation exchange resin. In addition, mixtures of different cation exchange resins can be used.

In another embodiment, the basic, anionic exchange resin is a tertiary amine anion exchange resin. Tertiary amine anion exchange resins contemplated for use in the practice of the invention include, for example, tertiary-aminated styrene-divinylbenzene copolymers, tertiary-aminated crosslinked styrene polymers, tertiary-aminated phenol-formaldehyde resins, tertiary-aminated benzene-formaldehyde resins, and mixtures thereof. In a further embodiment, the basic, anionic exchange resin is a quaternary amine anion exchange resin, or mixtures of these and other exchange resins.

The first and second ion exchange resins may contact the as-synthesized aqueous dispersion either simultaneously, or consecutively. For example, in one embodiment both resins are added simultaneously to an as-synthesized aqueous dispersion of an electrically conducting polymer, and allowed to remain in contact with the dispersion for at least about 1 hour, e.g., about 2 hours to about 20 hours. The ion exchange resins can then be removed from the dispersion by filtration. The size of the filter is chosen so that the relatively large ion exchange resin particles will be removed while the smaller dispersion particles will pass through. Without wishing to be bound by theory, it is believed that the ion exchange resins quench polymerization and effectively remove ionic and non-ionic impurities and most of unreacted monomer from the as-synthesized aqueous dispersion. Moreover, the basic, anion exchange and/or acidic, cation exchange resins renders the acidic sites more basic, resulting in increased pH of the dispersion. In general, about one to five grams of ion exchange resin is used per gram of new electrically conductive polymer composition.

In many cases, the basic ion exchange resin can be used to adjust the pH to the desired level. In some cases, the pH can be further adjusted with an aqueous basic solution such as a solution of sodium hydroxide, ammonium hydroxide, tetra-methylammonium hydroxide, or the like.

In another embodiment, more conductive dispersions are formed by the addition of highly conductive additives to the aqueous dispersions of the new electrically conductive polymer composition. Because dispersions with relatively high pH can be formed, the conductive additives, especially metal additives, are not attacked by the acid in the dispersion. Examples of suitable conductive additives include, but are not limited to metal particles and nanoparticles, nanowires, carbon nanotubes, graphite fibers or particles, carbon particles, and combinations thereof.

(iii) Electrochemical Polymerization

Electropolymerization techniques to form electrically conductive polymers are well known in the art. Typically, a one-compartment cell containing a reaction solvent, a polymeric supporting electrolyte and the monomer will be used. The non-fluorinated acid polymer functions as the supporting electrolyte. A conventional apparatus comprises working and counter electrodes. In some cases, a reference electrode is also present. Suitable working electrode materials include platinum, gold metal sheet, tin oxide on glass, indium tin oxide on glass, or other electrode materials that will allow the polymer to build up and to adhere and which will not be electrochemically corroded or damaged under the electropolymerization conditions. The working electrode can vary in shape or configuration, although a flat electrode will be preferred for the production thereon of a polymeric film. The counter electrode can be platinum, stainless steel, or other suitable material. The reference electrode can be an aqueous saturated calomel electrode or silver/silver nitrate reference electrode. Electropolymerization can be initiated by applying a potential difference between the working and counter electrodes. In some embodiments, the potential difference is 1-5 volts.

6. Fluorinated Acid Polymer

In some embodiments, the electrically conductive polymer composition further comprises a fluorinated acid polymer. The fluorinated acid polymer can be any polymer which is fluorinated and has groups with acidic protons. As used herein, the term "fluorinated" means that at least one hydrogen bonded to a carbon has been replaced with a fluorine. The term includes partially and fully fluorinated materials. In one embodiment, the fluorinated acid polymer is highly fluorinated. The term "highly fluorinated" means that at least 50% of the available hydrogens bonded to a carbon, have been replaced with fluorine. In some embodiments, at least 75% of the available hydrogens bonded to a carbon have been replaced with fluorine. The group having an acidic proton, is hereinafter referred to as an "acidic group." In one embodiment, the acidic group has a pKa of less than 3. In one embodiment, the acidic group has a pKa of less than 0. In one embodiment, the acidic group has a pKa of less than −5. The acidic group can be attached directly to the polymer backbone, or it can be attached to side chains on the polymer backbone. Examples of acidic groups include, but are not limited to, carboxylic acid groups, sulfonic acid groups, sulfonimide groups, phosphoric acid groups, phosphonic acid groups, and combinations thereof. The acidic groups can all be the same, or the polymer may have more than one type of acidic group.

In one embodiment, the fluorinated acid polymer is water-soluble. In one embodiment, the fluorinated acid polymer is dispersible in water.

In one embodiment, the fluorinated acid polymer is organic solvent wettable. The term "organic solvent wettable" refers to a material which, when formed into a film, is wettable by organic solvents. The term also includes polymeric acids which are not film-forming alone, but which form an electrically conductive polymer composition which is wettable. In one embodiment, wettable materials form films which are wettable by phenylhexane with a contact angle no greater than 40°. The methods for measuring contact angles are well known.

In one embodiment, the polymer backbone is fluorinated. Examples of suitable polymeric backbones include, but are not limited to, polyolefins, polyacrylates, polymethacrylates, polyimides, polyamides, polyaramids, polyacrylamides, polystyrenes, and copolymers thereof. In one embodiment, the polymer backbone is highly fluorinated. In one embodiment, the polymer backbone is fully fluorinated.

In one embodiment, the acidic groups are selected from sulfonic acid groups and sulfonimide groups. A sulfonimide group has the formula:

—$SO_2$—NH—$SO_2$—R where R is an alkyl group.

In one embodiment, the acidic groups are on a fluorinated side chain. In one embodiment, the fluorinated side chains are selected from alkyl groups, alkoxy groups, amido groups, ether groups, and combinations thereof.

In one embodiment, the fluorinated acid polymer has a fluorinated olefin backbone, with pendant fluorinated ether sulfonate, fluorinated ester sulfonate, or fluorinated ether sulfonimide groups. In one embodiment, the polymer is a copolymer of 1,1-difluoroethylene and 2-(1,1-difluoro-2-(trifluoromethyl)allyloxy)-1,1,2,2-tetrafluoroethanesulfonic acid. In one embodiment, the polymer is a copolymer of ethylene and 2-(2-(1,2,2-trifluorovinyloxy)-1,1,2,3,3,3-hexafluoropropoxy)-1,1,2,2-tetrafluoroethanesulfonic acid. These copolymers can be made as the corresponding sulfonyl fluoride polymer and then can be converted to the sulfonic acid form.

In one embodiment, the fluorinated acid polymer is homopolymer or copolymer of a fluorinated and partially sulfonated poly(arylene ether sulfone). The copolymer can be a block copolymer. Examples of comonomers include, but are not limited to butadiene, butylene, isobutylene, styrene, and combinations thereof.

In one embodiment, the fluorinated acid polymer is a homopolymer or copolymer of monomers having Formula VII of VIIa:

(VII)

[Structure: styrene with O(CF$_2$)$_b$SO$_2$R$^{13}$ substituent]

(VIIa)

[Structure: aniline with N$_3$ and O(CF$_2$)$_b$SO$_2$R$^{13}$ substituents]

where:

b is an integer from 1 to 5, $R^{13}$ is OH or $NHR^{14}$, and $R^{14}$ is alkyl, fluoroalkyl, sulfonylalkyl, or sulfonylfluoroalkyl.

In one embodiment, the monomer is "SFS" or "SFSI" shown below:

SFS

[Structure: styrene with OCF$_2$CF$_2$SO$_3$Li substituent]

SFSI

[Structure: styrene with OCF$_3$CF$_2$SO$_2$NSO$_2$CF$_2$ Li substituent]

After polymerization, the polymer can be converted to the acid form.

In one embodiment, the fluorinated acid polymer is a homopolymer or copolymer of a trifluorostyrene having acidic groups. In one embodiment, the trifluorostyrene monomer has Formula VIII:

(VIII)

[Structure: CF=CF$_2$ attached to phenyl with WSO$_2$R$^{13}$]

where:

W is selected from $(CF_2)_b$, $O(CF_2)_b$, $S(CF_2)_b$, $(CF_2)_bO(CF_2)_b$, b is independently an integer from 1 to 5, $R^{13}$ is OH or $NHR^{14}$, and $R^{14}$ is alkyl, fluoroalkyl, sulfonylalkyl, or sulfonylfluoroalkyl.

In one embodiment, the fluorinated acid polymer is a sulfonimide polymer having Formula IX:

(IX)

$$-\!\!\left(\!SO_2-R_f-SO_2-\underset{H}{N}\!\right)_{\!n}\!\!-$$

where:

$R_f$ is selected from fluorinated alkylene, fluorinated heteroalkylene, fluorinated arylene, and fluorinated heteroarylene; and n is at least 4.

In one embodiment of Formula IX, $R_f$ is a perfluoroalkyl group. In one embodiment, $R_f$ is a perfluorobutyl group. In one embodiment, $R_f$ contains ether oxygens. In one embodiment n is greater than 10.

In one embodiment, the fluorinated acid polymer comprises a fluorinated polymer backbone and a side chain having Formula X:

$$-OR^{15}-SO_2-NH-(SO_2-\underset{H}{N}-SO_2-\underset{H}{N})_a-SO_2R^{16} \quad (X)$$

where:
$R^{15}$ is a fluorinated alkylene group or a fluorinated heteroalkylene group;
$R^{16}$ is a fluorinated alkyl or a fluorinated aryl group; and
a is 0 or an integer from 1 to 4.

In one embodiment, the fluorinated acid polymer has Formula XI:

$$\left[-(CF_2-CF_2)_c-(CF_2-\underset{\underset{(CF_2-\underset{R^{16}}{CF}-O)_c-(CF_2)_c-SO_2-\underset{H}{N}-(SO_2-(CF_2)_c-SO_2-\underset{H}{N})_c-SO_2R^{16}}{O}}{CF})-\right]_n \quad (XI)$$

where:
$R^{16}$ is a fluorinated alkyl or a fluorinated aryl group;
c is independently 0 or an integer from 1 to 3; and
n is at least 4.

The synthesis of fluorinated acid polymers has been described in, for example, A. Feiring et al., J. Fluorine Chemistry 2000, 105, 129-135; A. Feiring et al., Macromolecules 2000, 33, 9262-9271; D. D. Desmarteau, J. Fluorine Chem. 1995, 72, 203-208; A. J. Appleby et al., J. Electrochem. Soc. 1993, 140(1), 109-111; and Desmarteau, U.S. Pat. No. 5,463,005.

In one embodiment, the fluorinated acid polymer comprises at least one repeat unit derived from an ethylenically unsaturated compound having the structure (XII):

(XII)

wherein d is 0, 1, or 2;
$R^{17}$ to $R^{20}$ are independently H, halogen, alkyl or alkoxy of 1 to 10 carbon atoms, Y, $C(R_f^t)(R_f^t)OR^{21}$, $R^4Y$ or $OR^4Y$;
Y is $COE^2$, $SO_2 E^2$, or sulfonimide;
$R^{21}$ is hydrogen or an acid-labile protecting group;
$R_f^t$ is the same or different at each occurrence and is a fluoroalkyl group of 1 to 10 carbon atoms, or taken together are $(CF_2)_e$ where e is 2 to 10;
$R^4$ is an alkylene group;
$E^2$ is OH, halogen, or $OR^5$; and
$R^5$ is an alkyl group;
with the proviso that at least one of $R^{17}$ to $R^{20}$ is Y, $R^4Y$ or $OR^4Y$.

$R^4$, $R^5$, and $R^{17}$ to $R^{20}$ may optionally be substituted by halogen or ether oxygen.

Some illustrative, but nonlimiting, examples of representative monomers of structure (XII) are presented below:

-continued wherein $R^{21}$ is a group capable of forming or rearranging to a tertiary cation, more typically an alkyl group of 1 to 20 carbon atoms, and most typically t-butyl.

Compounds of structure (XII) wherein d=0, structure (XII-a), may be prepared by the cycloaddition reaction of unsaturated compounds of structure (XIII) with quadricyclane (tetracyclo[2.2.1.0$^{2,6}$0$^{3,5}$]heptane) as shown in the equation below.

The reaction may be conducted at temperatures ranging from about 0° C. to about 200° C., more typically from about 30° C. to about 150° C. in the absence or presence of an inert solvent such as diethyl ether. For reactions conducted at or above the boiling point of one or more of the reagents or solvent, a closed reactor is typically used to avoid loss of volatile components. Compounds of structure (XII) with higher values of d (i.e., d=1 or 2) may be prepared by reaction of compounds of structure (XII) with d=0 with cyclopentadiene, as is known in the art.

In one embodiment, the fluorinated acid polymer also comprises a repeat unit derived from at least one ethylenically unsaturated compound containing at least one fluorine atom attached to an ethylenically unsaturated carbon. The fluoroolefin comprises 2 to 20 carbon atoms. Representative fluoroolefins include, but are not limited to, tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene-4-methyl-1,3-dioxolane), $CF_2=CFO(CF_2)_tCF=CF_2$, where t is 1 or 2, and $R_f''OCF=CF_2$ wherein $R_f''$ is a saturated fluoroalkyl group of from 1 to about ten carbon atoms. In one embodiment, the comonomer is tetrafluoroethylene.

In one embodiment, the fluorinated acid polymer comprises a polymeric backbone having pendant groups comprising siloxane sulfonic acid. In one embodiment, the siloxane pendant groups have the formula below:

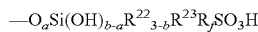

wherein:
a is from 1 to b;
b is from 1 to 3;
$R^{22}$ is a non-hydrolyzable group independently selected from the group consisting of alkyl, aryl, and arylalkyl;
$R^{23}$ is a bidentate alkylene radical, which may be substituted by one or more ether oxygen atoms, with the proviso that R23 has at least two carbon atoms linearly disposed between Si and $R_f$; and
$R_f$ is a perfluoralkylene radical, which may be substituted by one or more ether oxygen atoms.
In one embodiment, the fluorinated acid polymer having pendant siloxane groups has a fluorinated backbone. In one embodiment, the backbone is perfluorinated.

In one embodiment, the fluorinated acid polymer has a fluorinated backbone and pendant groups represented by the Formula (XIV)

$$—O_g—[CF(R_f^2)CF—O_h]_i—CF_2CF_2SO_3H \qquad (XIV)$$

wherein $R_f^2$ is F or a perfluoroalkyl radical having 1-10 carbon atoms either unsubstituted or substituted by one or more ether oxygen atoms, h=0 or 1, i=0 to 3, and g=0 or 1.

In one embodiment, the fluorinated acid polymer has formula (XV)

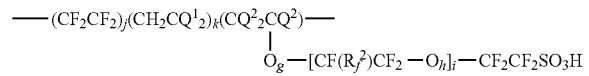
(XV)

where j≥0, k≥0 and 4≤(j+k)≤199, $Q^1$ and $Q^2$ are F or H, $R_f^2$ is F or a perfluoroalkyl radical having 1-10 carbon atoms either unsubstituted or substituted by one or more ether oxygen atoms, h=0 or 1, i=0 to 3, g=0 or 1. In one embodiment $R_f^2$ is —$CF_3$, g=1, h=1, and i=1. In one embodiment the pendant group is present at a concentration of 3-10 mol-%.

In one embodiment, $Q^1$ is H, k≥0, and $Q^2$ is F, which may be synthesized according to the teachings of Connolly et al., U.S. Pat. No. 3,282,875. In another preferred embodiment, $Q^1$ is H, $Q^2$ is H, g=0, $R_f^2$ is F, h=1, and i-1, which may be synthesized according to the teachings of co-pending application Ser. No. 60/105,662. Still other embodiments may be synthesized according to the various teachings in Drysdale et al., WO 9831716(A1), and co-pending US applications Choi et al, WO 99/52954(A1), and 60/176,881.

In one embodiment, the fluorinated acid polymer is a colloid-forming polymeric acid. As used herein, the term "colloid-forming" refers to materials which are insoluble in water, and form colloids when dispersed into an aqueous medium. The colloid-forming polymeric acids typically have a molecular weight in the range of about 10,000 to about 4,000,000. In one embodiment, the polymeric acids have a molecular weight of about 100,000 to about 2,000,000. Colloid particle size typically ranges from 2 nanometers (nm) to about 140 nm. In one embodiment, the colloids have a particle size of 2 nm to about 30 nm. Any colloid-forming polymeric material having acidic protons can be used. In one embodiment, the colloid-forming fluorinated polymeric acid has acidic groups selected from carboxylic groups, sulfonic acid groups, and sulfonimide groups. In one embodiment, the colloid-forming fluorinated polymeric acid is a polymeric sulfonic acid. In one embodiment, the colloid-forming polymeric sulfonic acid is perfluorinated. In one embodiment, the colloid-forming polymeric sulfonic acid is a perfluoroalkylenesulfonic acid.

In one embodiment, the colloid-forming polymeric acid is a highly-fluorinated sulfonic acid polymer ("FSA polymer"). "Highly fluorinated" means that at least about 50% of the total number of halogen and hydrogen atoms in the polymer are fluorine atoms, an in one embodiment at least about 75%, and in another embodiment at least about 90%. In one embodiment, the polymer is perfluorinated. The term "sulfonate functional group" (or simply "sulfonate") refers to either to sulfonic acid groups or salts of sulfonic acid groups, and in one embodiment alkali metal or ammonium salts. The functional group is represented by the formula —$SO_3E^5$ where $E^5$ is a cation, also known as a "counterion". $E^5$ may be H, Li, Na, K or $N(R_1)(R_2)(R_3)(R_4)$, and $R_1$, $R_2$, $R_3$, and $R_4$ are the same or different and are and in one embodiment H, $CH_3$ or $C_2H_5$. In another embodiment, $E^5$ is H, in which case the polymer is said to be in the "acid form". $E^5$ may also be multivalent, as represented by such ions as Ca++, and Al+++. It is clear to the skilled artisan that in the case of multivalent counterions, represented generally as $M^{x+}$, the number of sulfonate functional groups per counterion will be equal to the valence "x".

In one embodiment, the FSA polymer comprises a polymer backbone with recurring side chains attached to the backbone, the side chains carrying cation exchange groups. Polymers include homopolymers or copolymers of two or more monomers. Copolymers are typically formed from a nonfunctional monomer and a second monomer carrying the cation exchange group or its precursor, e.g., a sulfonyl fluoride group (—$SO_2F$), which can be subsequently hydrolyzed to a sulfonate functional group. For example, copolymers of a first fluorinated vinyl monomer together with a second fluorinated vinyl monomer having a sulfonyl fluoride group (—$SO_2F$) can be used. Possible first monomers include tetrafluoroethylene (TFE), hexafluoropropylene, vinyl fluoride, vinylidine fluoride, trifluoroethylene, chlorotrifluoroethylene, perfluoro(alkyl vinyl ether), and combinations thereof. TFE is a preferred first monomer.

In other embodiments, possible second monomers include fluorinated vinyl ethers with sulfonate functional groups or precursor groups which can provide the desired side chain in the polymer. Additional monomers, including ethylene, propylene, and R—CH=$CH_2$ where R is a perfluorinated alkyl group of 1 to 10 carbon atoms, can be incorporated into these polymers if desired. The polymers may be of the type referred to herein as random copolymers, that is copolymers made by polymerization in which the relative concentrations of the comonomers are kept as constant as possible, so that the distribution of the monomer units along the polymer chain is in accordance with their relative concentrations and relative reactivities. Less random copolymers, made by varying relative concentrations of monomers in the course of the polymerization, may also be used. Polymers of the type called block copolymers, such as that disclosed in European Patent Application No. 1 026 152 A1, may also be used.

In one embodiment, FSA polymers for include a highly fluorinated, and in one embodiment perfluorinated, carbon backbone and side chains represented by the formula —(O—CF$_2$CFR$_f^3$)$_a$-O—CF$_2$CFR$_f^4$SO$_3$E$^5$ wherein R$_f^3$ and R$_f^4$ are independently selected from F, Cl or a perfluorinated alkyl group having 1 to 10 carbon atoms, a=0, 1 or 2, and E$^5$ is H, Li, Na, K or N(R1)(R2)(R3)(R4) and R1, R2, R3, and R4 are the same or different and are and in one embodiment H, CH$_3$ or C$_2$H$_5$. In another embodiment E$^5$ is H. As stated above, E$^5$ may also be multivalent.

In one embodiment, the FSA polymers include, for example, polymers disclosed in U.S. Pat. No. 3,282,875 and in U.S. Pat. Nos. 4,358,545 and 4,940,525. An example of preferred FSA polymer comprises a perfluorocarbon backbone and the side chain represented by the formula

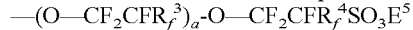
—O—CF$_2$CF(CF$_3$)—O—CF$_2$CF$_2$SO$_3$E$^5$ where X is as defined above. FSA polymers of this type are disclosed in U.S. Pat. No. 3,282,875 and can be made by copolymerization of tetrafluoroethylene (TFE) and the perfluorinated vinyl ether CF$_2$=CF—O—CF$_2$CF(CF$_3$)—O—CF$_2$CF$_2$SO$_2$F, perfluoro(3,6-dioxa-4-methyl-7-octenesulfonyl fluoride) (PDMOF), followed by conversion to sulfonate groups by hydrolysis of the sulfonyl fluoride groups and ion exchanged as necessary to convert them to the desired ionic form. An example of a polymer of the type disclosed in U.S. Pat. Nos. 4,358,545 and 4,940,525 has the side chain —O—CF$_2$CF$_2$SO$_3$E$^5$, wherein E$^5$ is as defined above. This polymer can be made by copolymerization of tetrafluoroethylene (TFE) and the perfluorinated vinyl ether CF$_2$=CF—O—CF$_2$CF$_2$SO$_2$F, perfluoro(3-oxa-4-pentene-sulfonyl fluoride) (POPF), followed by hydrolysis and further ion exchange as necessary.

In one embodiment, the FSA polymers have an ion exchange ratio of less than about 33. In this application, "ion exchange ratio" or "IXR" is defined as number of carbon atoms in the polymer backbone in relation to the cation exchange groups. Within the range of less than about 33, IXR can be varied as desired for the particular application. In one embodiment, the IXR is about 3 to about 33, and in another embodiment about 8 to about 23.

The cation exchange capacity of a polymer is often expressed in terms of equivalent weight (EW). For the purposes of this application, equivalent weight (EW) is defined to be the weight of the polymer in acid form required to neutralize one equivalent of sodium hydroxide. In the case of a sulfonate polymer where the polymer has a perfluorocarbon backbone and the side chain is —O—CF$_2$—CF(CF$_3$)—O—CF$_2$—CF$_2$—SO$_3$H (or a salt thereof), the equivalent weight range which corresponds to an IXR of about 8 to about 23 is about 750 EW to about 1500 EW. IXR for this polymer can be related to equivalent weight using the formula: 50 IXR+344=EW. While the same IXR range is used for sulfonate polymers disclosed in U.S. Pat. Nos. 4,358,545 and 4,940,525, e.g., the polymer having the side chain —O—CF$_2$CF$_2$SO$_3$H (or a salt thereof), the equivalent weight is somewhat lower because of the lower molecular weight of the monomer unit containing a cation exchange group. For the preferred IXR range of about 8 to about 23, the corresponding equivalent weight range is about 575 EW to about 1325 EW. IXR for this polymer can be related to equivalent weight using the formula: 50 IXR+178=EW.

The FSA polymers can be prepared as colloidal aqueous dispersions. They may also be in the form of dispersions in other media, examples of which include, but are not limited to, alcohol, water-soluble ethers, such as tetrahydrofuran, mixtures of water-soluble ethers, and combinations thereof. In making the dispersions, the polymer can be used in acid form. U.S. Pat. Nos. 4,433,082, 6,150,426 and WO 03/006537 disclose methods for making of aqueous alcoholic dispersions. After the dispersion is made, concentration and the dispersing liquid composition can be adjusted by methods known in the art.

Aqueous dispersions of the colloid-forming polymeric acids, including FSA polymers, typically have particle sizes as small as possible and an EW as small as possible, so long as a stable colloid is formed.

Aqueous dispersions of FSA polymer are available commercially as Nafion® dispersions, from E. I. du Pont de Nemours and Company (Wilmington, Del.).

Some of the polymers described hereinabove may be formed in non-acid form, e.g., as salts, esters, or sulfonyl fluorides. They will be converted to the acid form for the preparation of conductive compositions, described below.

7. Preparation of the Composite Dispersion

An aqueous dispersion of (a) a dihetero amine polymer doped with non-fluorinated polymeric acid and (b) a fluorinated acid polymer ("FAP") is referred to herein as a composite dispersion of the new electrically conductive polymer. The dihetero amine polymer has at least one monomeric unit derived from Formula II. In some embodiments, the dihetero amine polymer is a homopolymer having Formula II.

The composite dispersion is prepared by first forming the doped dihetero amine polymer and then adding the FAP. The FAP can be first dissolved or dispersed in an aqueous liquid.

The FAP is present in an amount such that the acid equivalent ratio of FAP to non-fluorinated polymeric acid is at least 0.2. In some embodiments, the ratio is no greater than 2.0.

In some embodiments, the pH is increased after the addition of the FAP. The pH can be adjusted by treatment with cation exchange resins and/or base resins prior to additive addition. In some embodiments, the pH is adjusted by the addition of aqueous base solution. Cations for the base can be, but are not limited to, alkali metal, alkaline earth metal, ammonium, and alkylammonium. In some embodiments, alkali metal is preferred over alkaline earth metal cations.

In some embodiments, the dispersion of the doped dihetero amine polymer and FAP is blended with other water soluble or dispersible materials. Examples of types of materials which can be added include, but are not limited to polymers, dyes, coating aids, organic and inorganic conductive inks and pastes, charge transport materials, crosslinking agents, and combinations thereof. The other water soluble or dispersible materials can be simple molecules or polymers.

The composite aqueous dispersions described herein can be formed into films. The films can be made using any liquid deposition technique, including continuous and discontinuous techniques. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

8. Buffer Layers

In another embodiment of the invention, there are provided buffer layers comprising the new electrically conductive polymer composition described herein. In some embodiments, the buffer layer consists essentially of an electrically conductive polymer having at least one monomeric unit derived from Formula II and doped with a non-fluorinated acid polymer. In some embodiments, the buffer layer consists essentially of (a) an electrically conductive polymer having at least one monomeric unit derived from Formula II and doped with a non-fluorinated acid polymer, and (b) a fluorinated acid polymer.

The dried films made from aqueous dispersions of the new electrically conductive polymer compositions are generally not redispersible in water. Thus the buffer layer can be formed as multiple thin layers. In addition, the buffer layer can be overcoated with a layer of different water-soluble or water-dispersible material without being damaged.

In another embodiment, there are provided buffer layers deposited from aqueous dispersions comprising the new electrically conductive polymer composition blended with other water soluble or dispersible materials. Examples of types of materials which can be added include, but are not limited to polymers, dyes, coating aids, organic and inorganic conductive inks and pastes, charge transport materials, crosslinking agents, and combinations thereof. The other water soluble or dispersible materials can be simple molecules or polymers.

9. Electronic Devices

In another embodiment of the invention, there are provided electronic devices comprising at least one electroactive layer positioned between two electrical contact layers, wherein the device further includes the new buffer layer. The term "electroactive" when referring to a layer or material is intended to mean a layer or material that exhibits electronic or electro-radiative properties. An electroactive layer material may emit radiation or exhibit a change in concentration of electron-hole pairs when receiving radiation.

As shown in FIG. 1, a typical device, 100, has an anode layer 110, a buffer layer 120, an electroactive layer 130, and a cathode layer 150. Adjacent to the cathode layer 150 is an optional electron-injection/transport layer 140.

The device may include a support or substrate (not shown) that can be adjacent to the anode layer 110 or the cathode layer 150. Most frequently, the support is adjacent the anode layer 110. The support can be flexible or rigid, organic or inorganic. Examples of support materials include, but are not limited to, glass, ceramic, metal, and plastic films.

The anode layer 110 is an electrode that is more efficient for injecting holes compared to the cathode layer 150. The anode can include materials containing a metal, mixed metal, alloy, metal oxide or mixed oxide. Suitable materials include the mixed oxides of the Group 2 elements (i.e., Be, Mg, Ca, Sr, Ba, Ra), the Group 11 elements, the elements in Groups 4, 5, and 6, and the Group 8-10 transition elements. If the anode layer 110 is to be light transmitting, mixed oxides of Groups 12, 13 and 14 elements, such as indium-tin-oxide, may be used. As used herein, the phrase "mixed oxide" refers to oxides having two or more different cations selected from the Group 2 elements or the Groups 12, 13, or 14 elements. Some non-limiting, specific examples of materials for anode layer 110 include, but are not limited to, indium-tin-oxide ("ITO"), indium-zinc-oxide, aluminum-tin-oxide, gold, silver, copper, and nickel. The anode may also comprise an organic material, especially an electrically conducting polymer such as polyaniline, including exemplary materials as described in "Flexible light-emitting diodes made from soluble conducting polymer," Nature vol. 357, pp 477 479 (11 Jun. 1992). At least one of the anode and cathode should be at least partially transparent to allow the generated light to be observed.

The anode layer 110 may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering, including ion beam sputtering, as well as e-beam evaporation and resistance evaporation. Specific forms of physical vapor deposition include rf magnetron sputtering and inductively-coupled plasma physical vapor deposition ("IMP-PVD"). These deposition techniques are well known within the semiconductor fabrication arts.

In one embodiment, the anode layer 110 is patterned during a lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet chemical or dry etching techniques. Other processes for patterning that are well known in the art can also be used.

The buffer layer 120 comprises the new electrically conductive polymer composition described herein. In some embodiments, the buffer layer consists essentially of the new electrically conductive polymer composition described herein. The layer can be formed using a variety of techniques well-known to those skilled in the art. In some embodiments, the layer is formed by deposition of aqueous dispersions of the new electrically conductive polymer composition, as described herein, using any of the liquid deposition techniques described above.

An optional layer, not shown, may be present between the buffer layer 120 and the electroactive layer 130. This layer may comprise hole transport materials.

Examples of hole transport materials have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules include, but are not limited to: 4,4',4"-tris(N,N-diphenyl-amino)triphenylamine (TDATA); 4,4',4"-tris(N-3-methylphenyl-N-phenyl-amino)triphenylamine (MTDATA); N,N'-diphenyl-N,N'-bis(3-methylphenyl)[1,1'-biphenyl]-4, 4'-diamine (TPD); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl]pyrazoline (PPR or DEASP); 1,2-trans-bis (9H-carbazol-9-yl)cyclobutane (DCZB); N,N,N',N'-tetrakis (4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the electroactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). In one embodiment, the electroactive material is an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, naphthalene, anthracene, chrysene, pyrene, tetracene, xanthene, perylene, coumarin, rhodamine, quinacridone, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Optional layer 140 is an electron transport layer. Examples of electron transport materials which can be used in the optional electron transport layer 140, include metal chelated oxinoid compounds, such as tris(8-hydroxyquinolato)aluminum (AlQ), bis(2-methyl-8-quinolinolato)(p-phenylphenolato)aluminum (BAlq), tetrakis-(8-hydroxyquinolato)hafnium (HfQ) and tetrakis-(8-hydroxyquinolato) zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. The electron-transport layer may also be doped with n-dopants, such as Cs or other alkali metals.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds such as LiF, $Li_2O$ or CsF can also be deposited between the organic layer and the cathode layer to lower the operating voltage. This layer may be referred to as an electron injection layer.

It is understood that each functional layer can be made up of more than one layer.

In some embodiments, an encapsulation layer (not shown) is deposited over the contact layer 150 to prevent entry of undesirable components, such as water and oxygen, into the device 100. Such components can have a deleterious effect on the organic layer 130. In one embodiment, the encapsulation layer is a barrier layer or film. In one embodiment, the encapsulation layer is a glass lid.

Though not depicted, it is understood that the device 100 may comprise additional layers. Other layers that are known in the art or otherwise may be used. In addition, any of the above-described layers may comprise two or more sub-layers or may form a laminar structure. Alternatively, some or all of anode layer 110 the hole transport layer 120, the electron transport layer 140, cathode layer 150, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

Figure 2:
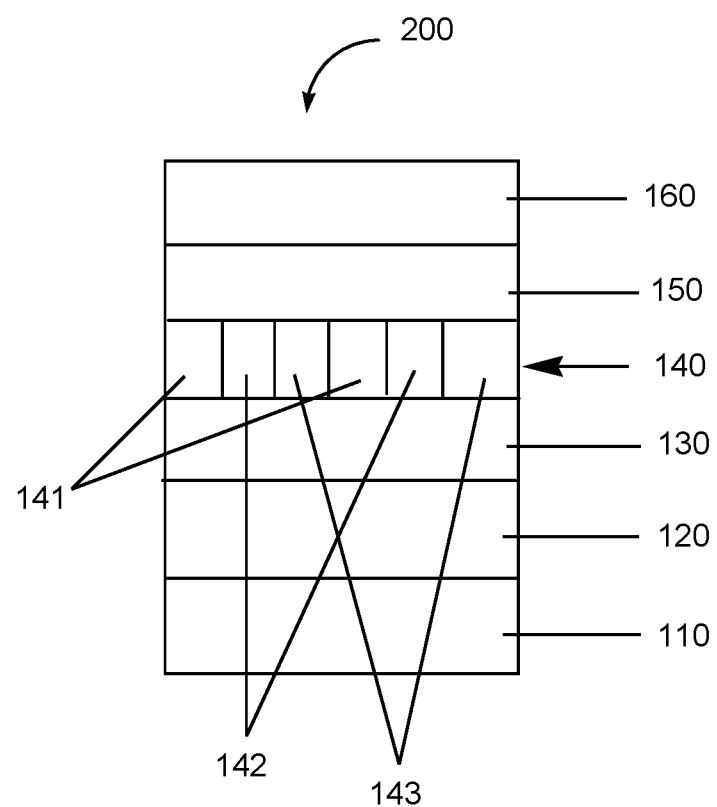
FIG. 2 includes an illustration of an exemplary organic device including a new compound or polymer described herein.

In some embodiments, in order to achieve full color, the light-emitting layer is pixellated, with subpixel units for each of the different colors. An illustration of a pixellated device is shown in FIG. 2. The device 200 has anode 110, hole injection layer 120, hole transport layer 130, electroluminescent layer 140, electron transport layer 150, and cathode 160. The electroluminescent layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In one embodiment, the different layers have the following range of thicknesses: anode 110, 500-5000 Å, in one embodiment 1000-2000 Å;

buffer layer 120, 50-2000 Å, in one embodiment 200-1000 Å; photoactive layer 130, 10-2000 Å, in one embodiment 100-1000 Å; optional electron transport layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer.

The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

EXAMPLES

The concepts described herein will be further described in the following examples, which do not limit the scope of the invention described in the claims.

Synthesis Example 1

This example illustrates the preparation of intermediate compounds A and B.

1

COMPOUND A

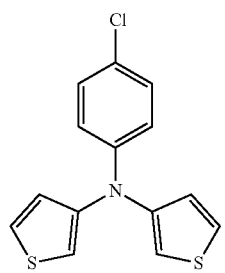

COMPOUND B

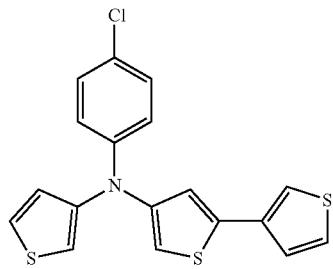

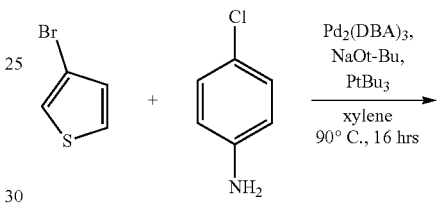

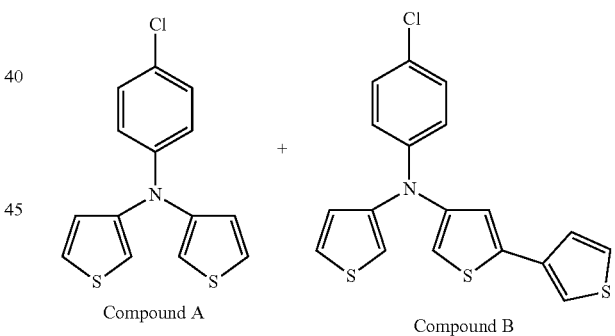

Compound A    Compound B

To a 200 mL round bottom flask under nitrogen were added 3-bromothiophene (3.00 g, 18.40 mmol), 4-chloroaniline (1.15 g, 9.02 mmol), palladium(II) acetate (0.203 g, 0.902 mmol), tri-tent-butyl phosphine (0.183 g, 0.902 mmol) and anhydrous xylene (30 mL). Once all the starting materials were dissolved, sodium t-butoxide (1.19 g, 19.85 mmol) was added and the resulting mixture was heated to 90° C. for sixteen hours.

The solution was cooled to room temperature and then quenched with ~50mL of water. The layers were separated, the organic layer was dried over $NaSO_4$, and the crude material was purified using silica chromatography with hexane:DCM—0-20% as the eluent. Compound A was obtained as an off-white solid in 18% yield (1.0 g). Compound B was obtained as a yellow oil in 9% yield (0.636 g).

Synthesis Example 2

This example illustrates the preparation of Compound I-4.

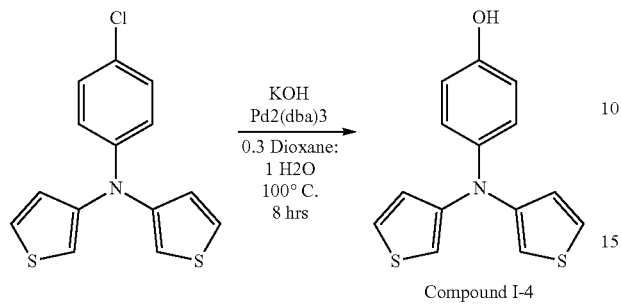

Compound I-4

To a 40 mL scintillation vial under nitrogen were added Compound A (1.00 g, 3.43 mmol), and potassium hydroxide (3.29 g, 34.3 mmol) and 1:2 dioxane:water (9 mL). The solution was degassed. Tris(dibenzylideneacetone)dipalladium(0) (0.063 g, 0.039 mmol), and 2-Di-tert-butylphosphino-3,4,5,6-tetramethyl-2',4',6'-triisopropyl-1,1'-biphenyl (0.132 g, 0.274 mmol) were premixed in dioxane (5 mL) and added to the stirring solution via syringe. The resulting mixture was heated to 100° C. for sixteen hours. The layers were separated, the organic layer was dried over $NaSO_4$, and the crude material was purified using silica chromatography hexane:ethylacetate—0-100% as the eluent. The desired product was obtained as a beige solid in 31% yield (0.285 g).

Synthesis Example 3

This example illustrates the preparation of Compound I-3.

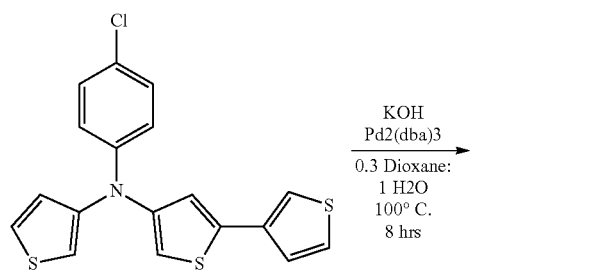

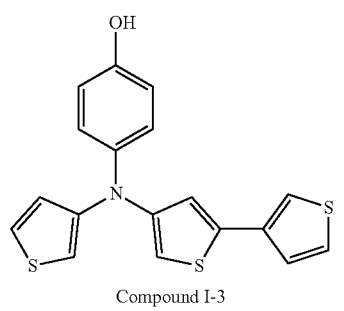

Compound I-3

Synthesis of compound I-3 was performed as described for compound I-4 but using Compound B. The crude material was purified using silica chromatography with hexane: ethylacetate—0-100% as the eluent The desired product was isolated in 23% yield (0.138 g).

Synthesis Example 4

This example illustrates the synthesis of Compound I-2.

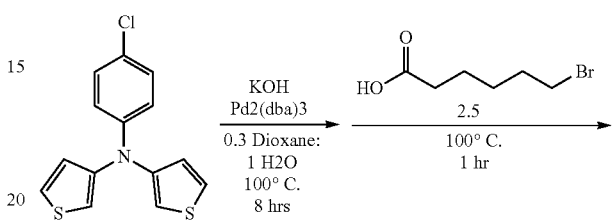

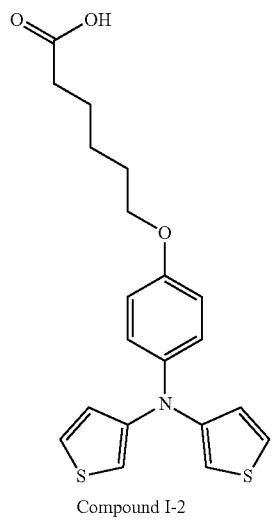

Compound I-2

To a 40 mL scintillation vial under nitrogen were added Compound A (1.00 g, 3.43 mmol), and potassium hydroxide (3.29 g, 34.3 mmol) and 1:2 dioxane:water (15 mL). The solution was degassed. Tris(dibenzylideneacetone)dipalladium(0) (0.062 g, 0.069 mmol), and 2-Di-tert-butylphosphino-3,4,5,6-tetramethyl-2',4',6'-triisopropyl-1,1'-biphenyl (0.274 g, 0.08 mmol) were premixed in dioxane (5 mL) and added to the stirring solution via syringe. The resulting mixture was heated to 100° C. for sixteen hours. 6-Bromohexanoic acid (2.22 g, 8.22 mmol) was added to the solution and the mixture was stirred for 1 hr. An additional equivalent of 6-Bromohexanoic acid was added to drive the reaction to completion. After an additional 1 hr at 100° C., the solution was cooled to room temperature. The layers were separated, the organic layer was dried over $NaSO_4$, and the crude material was purified using silica chromatography with hexane:DCM—0-100% as the eluent followed by DCM: DCM10% EtOH—0-40% as the eluent. The desired product was obtained as a brown oil in 23% yield (0.304 g).

Synthesis Example 5

This example illustrates the preparation of Compound I-1.

(a) Synthesis of intermediate Compound F

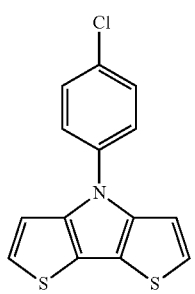

COMPOUND F

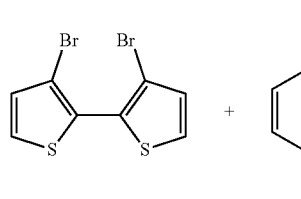

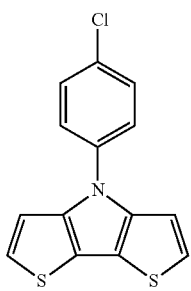 [SMILES: Clc1ccc(-n2c3ccsc3c3sccc32)cc1]

To a 40 mL scintillation vial under nitrogen were added 3,3-dibromo-2,2-bithiophene (2.00 g, 6.17 mmol), 4-chloroanaline (0.819 g, 6.42 mmol), tris(dibenzylideneacetone)dipalladium(0) (0.141 g, 0.154 mmol), tri-tent-butyl phosphine (0.062 g, 0.309 mmol) and and anhydrous toluene (20 mL). Once all the starting materials were dissolved, sodium t-butoxide (1.42 g, 14.8 mmol) was added and the resulting mixture was heated to 100° C. for thirty-six hours. The solution was cooled to room temperature and then quenched with ~50 mL of water. The layers were separated, the organic layer was washed with water (50 mL), 0.01 M citric acid (50 mL) and saturated sodium carbonate (50 mL), sodium thiosulfate solution (50 mL) and brine (50 mL), and dried over $NaSO_4$; and the crude material was purified using silica chromatography with hexane:DCM—0-10% as the eluent. Compound F was obtained as a white solid in 18% yield (1.0 g). Compound B was obtained as a yellow oil in 21.5% yield (0.365 g).

(b) Synthesis of Compound I -1

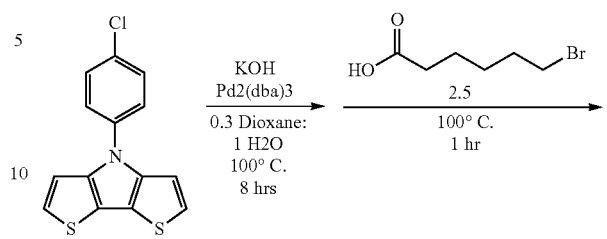

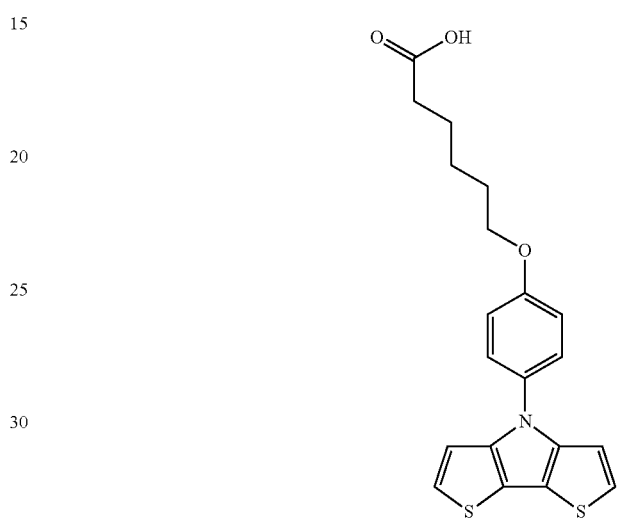

Compound I-1

Synthesis of compound I-1 was performed as described for compound I-2 but using Compound F. The desired product was isolated as a white solid in 41% yield (0.200 g).

Synthesis Example 6

This example illustrates the preparation of Polymer II-1.

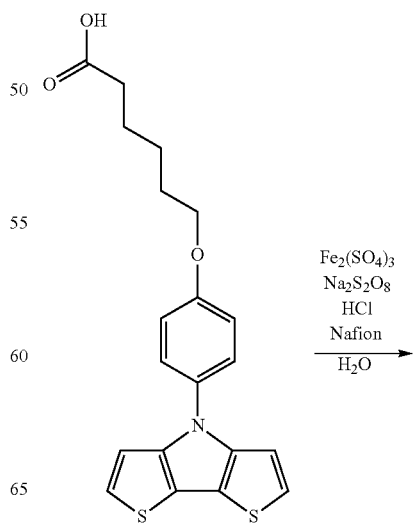

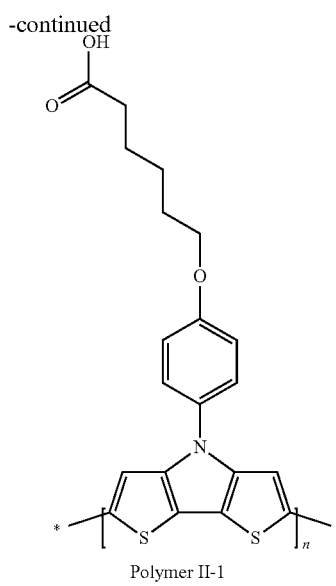

Polymer II-1

To a 100 ml round-bottom flask were added 7.07 g Nafion (EW=1000) and 10.86 g of DI water. After stirring for 30 min 1.03 mg $Fe_2(SO_4)_3$ (from stock solution) and 12.7 μl conc HCl were added, followed by the addition of a solution of 0.077 g of $Na_2S_2O_8$ in 5 g of DI water. After heating RM to 60° C., 0.100 g of Compound I-1 was added portion-wise during 5 min. After 16 hrs, the reaction was quenched by adding it to 2.5 g of Dowex M43, 2.5 g of Dowex M31(H+) and 2.5 g of DI water. The mixture was placed on a roller/mixer for 30 min, filtered and the filtrate subsequently added to 2.5 g of Dowex M31(Na+) and 1.25 g of DI water. The mixture was placed on a roller/mixer for 30 min and filtered. The filtrate was collected as a brown/blue liquid.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A homopolymer having formula II

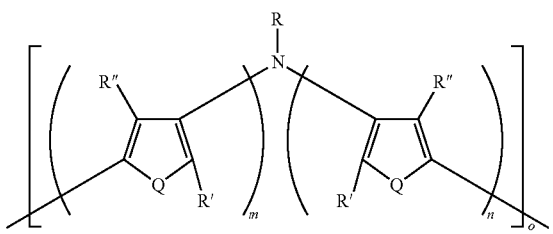

(II)

wherein:

Q=S;

R is selected from the group consisting of alkoxy, ether, polyether, fluoroalkyl, aryl, aryloxy, heteroaryl, silyl, siloxane, siloxy, germyl, deuterated partially-fluorinated alkyl, deuterated alkoxy, deuterated ether, deuterated polyether, deuterated aryl, deuterated heteroaryl, deuterated silyl, deuterated siloxane, deuterated siloxy, and deuterated germyl, wherein R is terminated by a carboxylic acid;

R' together represent a single bond which forms a fused ring;

R" is H;

m=n=1; and o is an integer from 2-2000.

2. The homopolymer of claim 1, wherein R is selected from the group consisting of aryl and deuterated aryl, wherein R is terminated by a carboxylic acid.

3. The homopolymer of claim 1, wherein o=10-2000.

* * * * *